United States Patent [19]

Fukuhara et al.

[11] Patent Number: 5,322,786

[45] Date of Patent: * Jun. 21, 1994

[54] METHOD OF REGULATING EXPRESSION OF A FOREIGN GENE BY CONTROLLING CULTURE TEMPERATURE AND A PROCESS OF PRODUCING A FOREIGN GENE PRODUCT THEREBY

[75] Inventors: Nobuhiro Fukuhara, Ohmuta; Setsuo Yoshino, Yokohama; Kaoru Yamamoto, Yokohama; Satori Sone, Yokohama; Maki Suzuki, Yokohama; Yoshiyuki Nakajima, Yokohama, all of Japan

[73] Assignee: Mitsui Toatsu Chemicals, Incorporated, Tokyo, Japan

[ * ] Notice: The portion of the term of this patent subsequent to Aug. 27, 2008 has been disclaimed.

[21] Appl. No.: 798,044

[22] Filed: Nov. 27, 1991

Related U.S. Application Data

[60] Continuation-in-part of Ser. No. 710,835, Jun. 5, 1991, abandoned, which is a division of Ser. No. 156,814, Feb. 17, 1988, Pat. No. 5,043,277.

[30] Foreign Application Priority Data

Feb. 19, 1987 [JP] Japan .................................. 62-034397
Jun. 18, 1987 [JP] Japan .................................. 62-152359

[51] Int. Cl.$^5$ .................... C12N 9/88; C12N 15/00; C12N 1/21; C12N 15/63
[52] U.S. Cl. ................................ 435/232; 435/172.3; 435/252.33; 435/320.1
[58] Field of Search ............... 435/69.1, 172.3, 252.3, 435/252.33, 320.1, 232

[56] References Cited

FOREIGN PATENT DOCUMENTS

| | | | |
|---|---|---|---|
| 0152613 | 8/1985 | European Pat. Off. | C12N 15/00 |
| 0260919 | 3/1988 | European Pat. Off. | C12N 15/00 |
| WO88/02024 | 3/1988 | PCT Int'l Appl. | C12N 15/00 |

OTHER PUBLICATIONS

Gilbert et al, Journal of Bacterology, vol. 161, No. 1, pp. 314–320, Jan. 1985.
Anson et al., Gene, vol. 58, Nos. 2-3, pp. 189-199, 1987.
Mieschendal et al, Biotechnology, vol. 4, No. 9, pp. 802-808 1986.
Remaut et al. Gene, vol. 15, pp. 81-93, 1981.
Remaut et al, Nucelic Acids Research, vol. 11, No. 14, pp. 4677–4688, 1983.
Nichols et al, Methods in Enzymology, vol. 101, pp. 155-164, 1983.
de Boer et al, Proc. Natl. Sci. USA, vol. 80, pp. 21-25, 1983.
Amann et al, Gene, vo. 25, No. 2/3, pp. 167-178, Nov. 1983.

Primary Examiner—Richard A. Schwartz
Assistant Examiner—Nancy T. Vogel
Attorney, Agent, or Firm—Nixon & Vanderhye

[57] ABSTRACT

*Escherichia coil* carrying a hybrid plasmid having been constructed by inserting a desired foreign gene into an expression vector so as to permitting expression of said desired foreign gene therein was cultured at a temperature 40° C. or over so that the expression of said desired foreign gene was suppressed. This E. coil (i.e., transformant) was cultured at 40° C. or over in a first process to suppress the expression of the foreign gene and to support sufficient cell growth and thereafter below 40° C. in a second process to release the suppression of the expression so as to permit effective production of the foreign gene product, which resulted in high concentration of the foreign gene product in the final culture.

6 Claims, 16 Drawing Sheets

FIG. 2(A)

```
         10        20        30        40        50        60
ATGGCACCCTCGGCTTCGACTCGATCTCGCACTCGTTCGCAAACGGGCGTCGCATCCGCAAAG
         70        80        90       100       110       120
CAGGCTGTCAATGGGCGCCTCGACCAACCTCGACCAGTCGCAGGCTCGCACCTGCCCACAACC
        130       140       150       160       170       180
CAGGTCACGCAGGTCGACATCGTCGAGAAGATGCTCGCGCCGACCGAGACTCGACGCTC
        190       200       210       220       230       240
GAACTCGAGACGGGCTACTCGCTCAACCTCGGAGACGTCGTCTCGGCCGCGAGGAAGGGCAGG
        250       260       270       280       290       300
CCTGTCCGCGTCAAGGACAGCGACGAGATCCGCTCAAAGATTGACAAATCGGTCGAGTTC
        310       320       330       340       350       360
TTGCGGCTCGCAACTCTCCATGAGCGTCTACGGCGTCACGACTGGATTGGGCGGATCCGCA
        370       380       390       400       410       420
GACACCCGACCGAGGACGCCATCTCGCTCCAGAAGGCTCTCCTCGAGCACCAGCTCTGC
        430       440       450       460       470       480
GGTGTTCTCCCTTCGACTCGTTCGACTCGGCCCTTCCGACTCGGCGTCTCGAGAACTCGCTT
        490       500       510       520       530       540
CCCCTCGAGGTTGTTCGCGGCGCCATGACAATCCGCGTCAACAGCTTGACCCGGCCAC
        550       560       570       580       590       600
TCGGCTGTCCGCCTCGTCCCTCGAGGGCTCACCAACTTCCTCAACCACGGCATCACC
```

FIG. 2(B)

```
         610                620                630                640                650                660
CCCATCGTCCCCCTCCGGCACCATCTCTGCGTCGGGCGACCCTCTCCTCTCCTAC
         670                680                690                700                710                720
ATTGCAGCGGGCCATCAGCGGTCACCCGGACAGCAAGGTGCACGTCGTCCAGGACCAAG
         730                740                750                760                770                780
GAGAAGATCCTGTACGCCCCGCGAGGCGATGGCGCTCTCTTCAACCTCGAGCCCGTCGTCCTC
         790                800                810                820                830                840
GGCCCGAAGGAAGGTCTCGGTCTCGTCAACGGCACCGTCTCAGCATCGATGGCCACC
         850                860                870                880                890                900
CTCGGCTCTGCACGACGCACACATGCTCTCGCTCTCCTCGCAGTCGCTCACGGCCATGACG
         910                920                930                940                950                960
GTCGAAGCGATGGTCGGCACGCCGGTCGTTCCACCCTTCCTTCAGGACGTCACGCGC
         970                980                990               1000               1010               1020
CCTCACCCGACGCAGATCGAAGTCGCGGGAAACATCCGCAAGCTCCTCGAGGGAAGCCGC
        1030               1040               1050               1060               1070               1080
TTTGCTGTCCACCATGAGGAGGAGGTCAAGGTCAAGGACGAGGCATTCTCCGCCAG
        1090               1100               1110               1120               1130               1140
GACCGCTACCCCTTGCCACGTCTCCCTCAGTGGCTCGGCCCGCTCGTCAGCGACCTCATT
        1150               1160               1170               1180               1190               1200
CACGCCCAGCCCGTCCTCACCATCGAGGCCCAGTGCCGGCGACCGACAACCCTCTCATC
```

FIG. 2(C)

```
         1210      1220      1230      1240      1250      1260
GACGTCGAGAACAAGACTTCGCACCACGGGGGCAATTTCCAGGCTGCCGCTGTGGCCAAC
         1270      1280      1290      1300      1310      1320
ACCATGGAGAAGACTCGCCTCGGGCTCGCCCAGATCGGCAAGCTCAACTTCACGCAGCTC
         1330      1340      1350      1360      1370      1380
ACCGAGATGCTCAACGCCGGGCATGAACGGGCCCTCCCCTGCCTCGGCCGGAAGAC
         1390      1400      1410      1420      1430      1440
CCCTCGCTCTCCTACCACTGCAAGGGCCTCGACATCGCCTGCGGGTACACCTCGGAG
         1450      1460      1470      1480      1490      1500
TTGGGACAACCTCGCCAAACCCCTGTGACGACGCATGTCCAGCCGGCTGAGATGGGCGAACCAG
         1510      1520      1530      1540      1550      1560
GCGGTCAACTCGCTTGCGCTCATCTCGGCTCGTCGCACGACCGAGTCCAACGACGTCCTT
         1570      1580      1590      1600      1610      1620
TCTCTCCTCCGGCCACCGAGTTTCTCCAAGCCATGCGTTGACTTGCCGCGCGATC
         1630      1640      1650      1660      1670      1680
GAGTTCGAGTTCAAGAAGCAGTTCGGCCCAGCCATCGTCTCGCTCATCGACCAGCACTTT
         1690      1700      1710      1720      1730      1740
GGCTCCGCCATGACCGGCTCGAAACCTGCCGACGAGCTCGTCGAGAAGGTGAACAAGACG
         1750      1760      1770      1780      1790      1800
CTCGCCAAGCGCCTCGAGCAGAGACCAACCTCGTACGACCTCGTCCCCGCTGGCCACGACGCC
```

FIG. 2(D)

```
          1810      1820      1830      1840      1850      1860
TTCTCCTTCGCCGCCGGCACCGTCGTCGAGGTCCTCTCGTCGACGTCGCTCTCGCTCGCC
          1870      1880      1890      1900      1910      1920
GCCGTCAACGCCCTGGAAGGTCGGCCGGCCGAGTCGGCCATCTCGCTCACCCGCCAAGTC
          1930      1940      1950      1960      1970      1980
GCGGAGACCTTCTGGTCCGCCGTCGACCTCGTCGCGCGCTCTCGTACCTCTCGCCG
          1990      2000      2010      2020      2030      2040
CGCACTCAGATCCCTCTACGCCTTCGTCCGGAGGAGCTTGGCGTCAAGGCCCGCCGGA
          2050      2060      2070      2080      2090      2100
GACGTCTTCCTCGGCAAGCAAGAGGTGACGATCGGCTCGAACGTCTCCAAGATCTACGAG
          2110      2120      2130      2140      2150
GCCATCAAGTCGGGCAGGATCAACAACGTCCCTCCTCGCTTAGACACTCTTC

CCACTCTCGCATCCCCTATCCCCGCCCTGCACTCTTAGGACTCGCTTCTTGTC

GGACTCGGATCTCGCATCGCTTTCTTGCCCTCTCTAGACCGTGTCGGTAT

TACCTCGAGATTGTGAATACAAGCAGTACCCATCCAAAAAAAAAAAAA
```

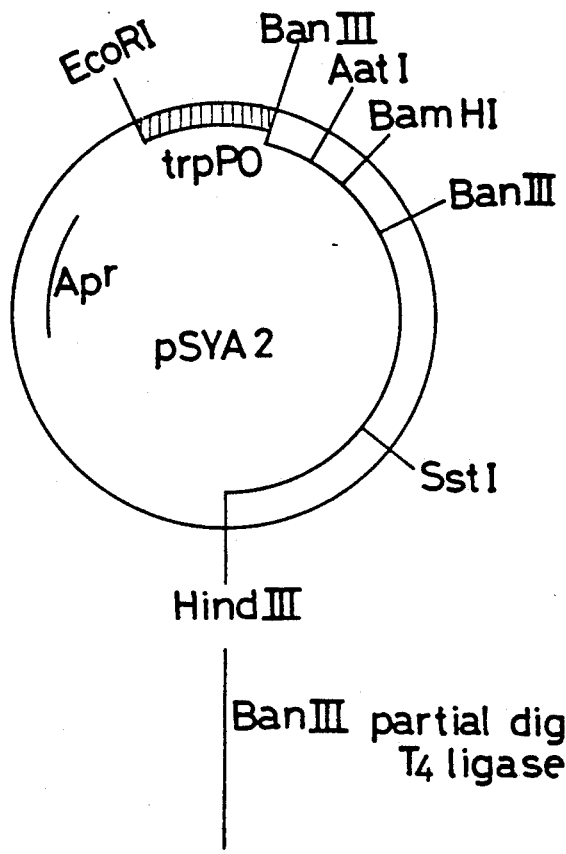
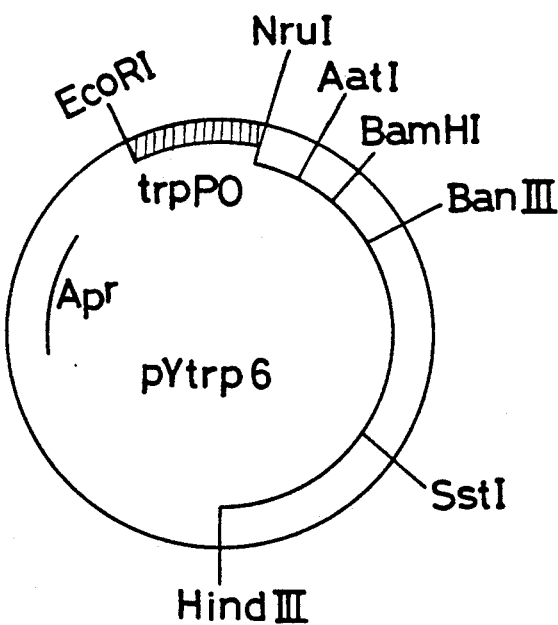
FIG. 7

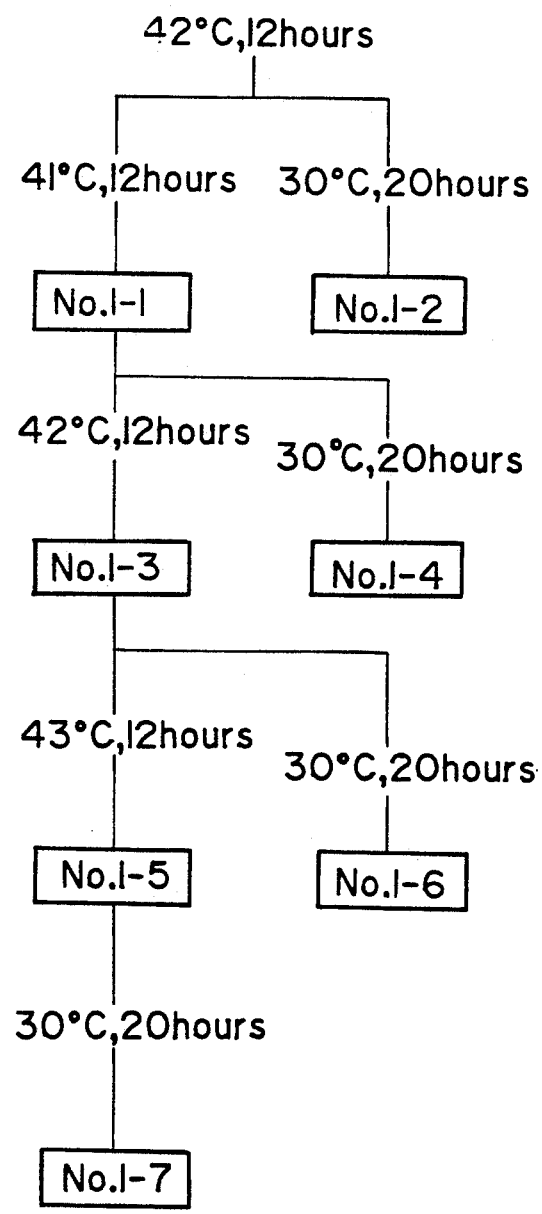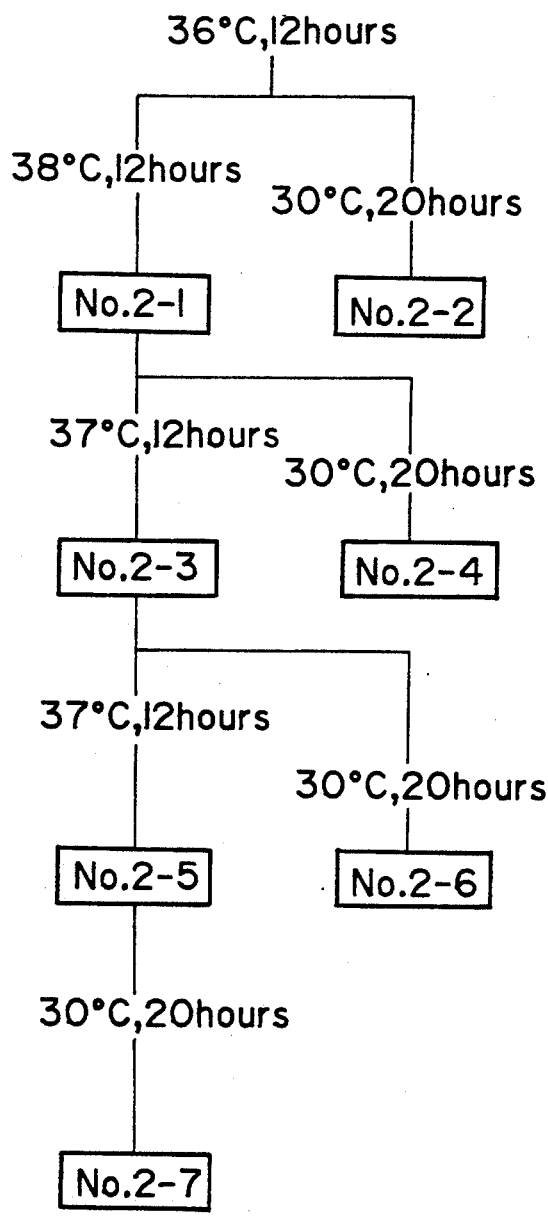

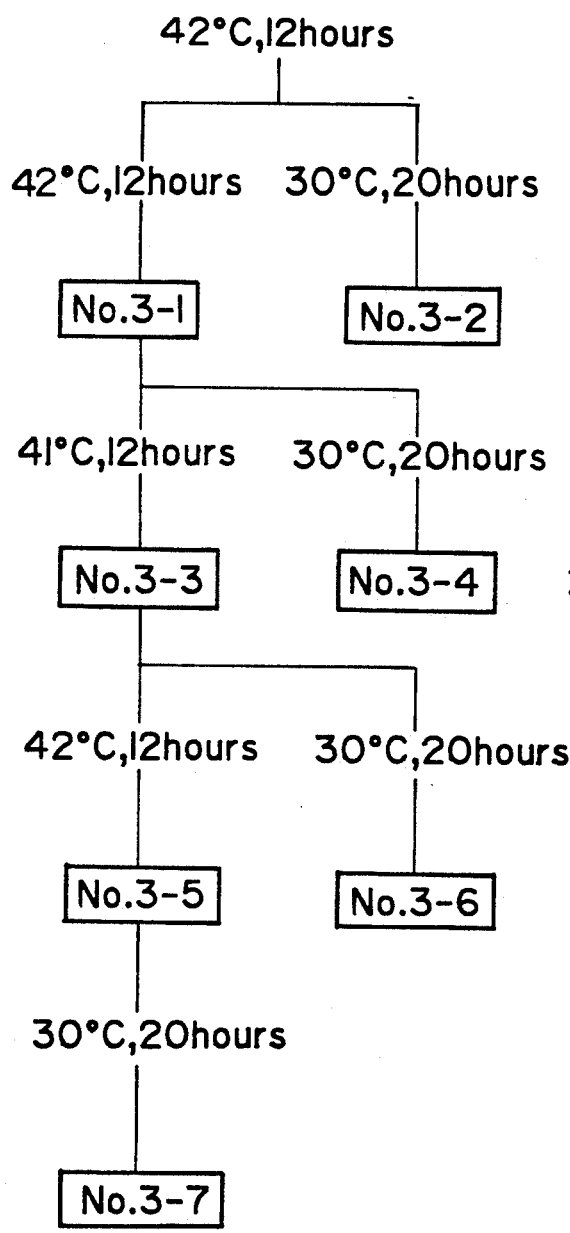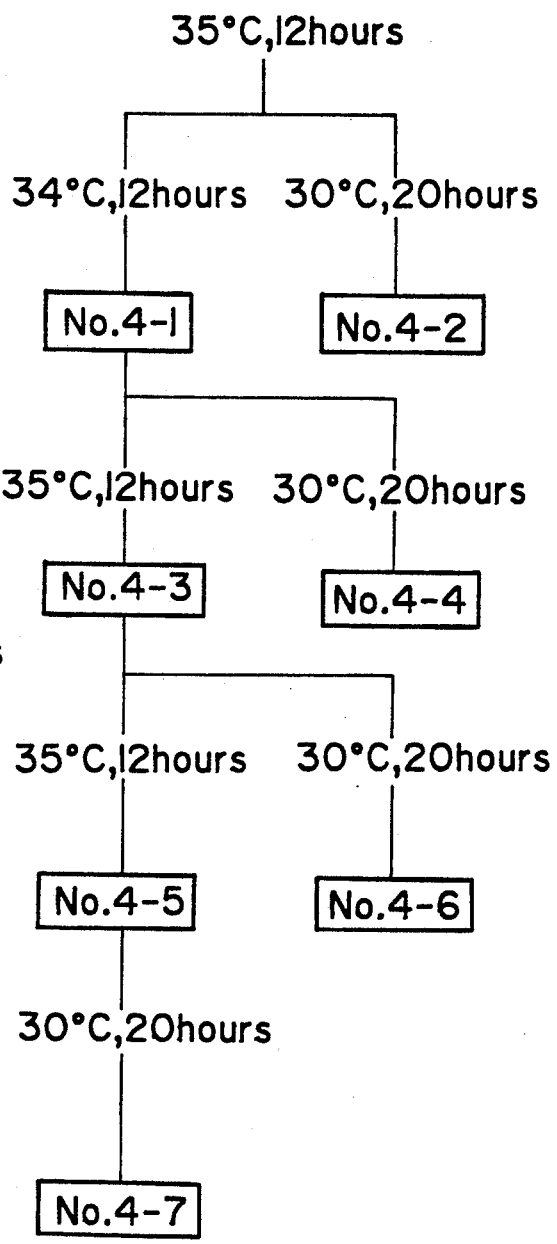
FIG.14
FIG.15

METHOD OF REGULATING EXPRESSION OF A FOREIGN GENE BY CONTROLLING CULTURE TEMPERATURE AND A PROCESS OF PRODUCING A FOREIGN GENE PRODUCT THEREBY

This is a continuation-in-part of application Ser. No. 07/710,835, filed Jun. 5, 1991, now abandoned which is a division of Ser. No. 07/156,814 filed Feb. 17, 1988, now U.S. Pat. No. 5,043,277.

BACKGROUND OF THE INVENTION

1. Field of the Invention

This invention relates to a useful method of regulating expression of a desired foreign gene, in which *Escherichia coli* carrying a recombinant plasmid (hybrid plasmid) with an insertion of said foreign gene therein grows efficiently whereas the expression of said foreign gene is efficiently suppressed. This invention also relates to a process of producing a foreign gene product by using said regulating method in which the period of the growth of *E. coil* carrying the hybrid plasmid therein is separated from the period of the expression of the foreign gene.

2. Description of the Prior Art

Currently, in virtue of the progress of gene recombination technology, a method has been developed for producing a desired foreign polypeptide in a host bacterium, in which a hybrid plasmid is constructed by inserting a structural gene, which originates from the animals, plants or microorganisms and encodes for the desired foreign polypeptide, into an expression vector which permits the expression of the foreign gene in the host bacterium and then the host bacterium is cultured to produce the desired foreign gene product.

This technology has almost established the measures for producing useful substances, such as human insulin and human growth hormones in large amounts.

As host bacteria for producing products of the foreign genes in such gene recombination technology, strains of *Echerichia coli* are widely used because their biological characteristics have been sufficiently investigated and, further they have no known pathogenicity and can easily grow in culture media having relatively simple compositions.

In general, however, the stability of the hybrid plasmid incorporated into *E. coil* spp. is not necessarily high so that deletion of the hybrid plasmid from *E. coli* or change in construction of the hybrid plasmid occurs during the period of cell growth, which results in high incidence of hybrid-plasmid-deleted cells bearing no capability in expressing foreign genes.

For example, in the industrial scale production, where mass culture is to be carried out, relatively long incubation time is generally required even in the preliminary culture to obtain a sufficient number of bacterial cells with high activity for the use in the following main bulk culture. Thus, high incidence of the deletion of hybrid plasmids from the bacterial cells as mentioned above can not be avoided. In consequence, the number of the effective foreign genes in the culture decreases as the number of the hybrid-plasmid-deleted cells increases, which results in a poor yield of the desired foreign gene product in the final culture.

In view of the aforementioned problem caused by the use of the hybrid plasmid in the culture, the method of separating the period of cell growth from that of gene expression has been brought into discussion.

More precisely, the method comprises culturing a host bacterium carrying a hybrid plasmid with an insertion of a foreign gene therein under the conditions such that the expression of the foreign gene in the hybrid plasmid is suppressed until a desired number of cells be obtained and thereafter the suppression be released to permit the expression of the foreign gene and the culture be continued. In consequence, the incidence of hybrid-plasmid-deleted cells is suppressed as low as possible so that the foreign gene product are efficiently produced.

A known example of the method of controlling expression of a foreign gene as such comprises the use of an inducible-type expression promoter as the hybrid plasmid so that the expression of the foreign gene can voluntarily induced by addition of an inducer which inactivates repressors such as the $p_L$lambda promoter/operator of the *E. coil* lambda phage or the trp-promoter/operator of the *E. coil* tryptophan operon.

Another known example of the method of controlling expression of a foreign gene comprises the use of a temperature-dependent-type vector which has a temperature-dependent replication origin (i.e., the vector starts replication only at a certain range of specified temperatures) and thus the foreign gene expression is regulated by changing the culture temperature.

However, in the case of using the inducible-type expression promoter, the production cost tends to be high since the expression inducers are expensive and furthermore, the incidence of the hybrid-plasmid-deleted bacteria cannot be sufficiently prevented. Consequently, the method cannot be applicable to the industrial scale culture.

Furthermore, in the case of using the temperature-dependent-type vector, the incidence of the hybrid-plasmid-deleted bacteria cannot be prevented effectively.

SUMMARY OF THE INVENTION

In view of the above-mentioned problems and in quest of establishing more effective means to produce foreign gene products, the present inventors have made several investigations in terms of fermentation technology with regards to the characteristics of *E. coli* carrying hybrid plasmids therein. In the course of the investigations, it was found out that expression of a foreign gene incorporated in a hybrid plasmid in *E. coli* was effectively controlled simply by regulating the culture temperature of *E. coli* carrying the hybrid plasmid with the foreign gene inserted therein.

Furthermore, the present invention was based on the conclusion that in the production of a foreign gene product by culturing bacteria carrying the hybrid plasmid introduced therein, it is possible to obtain the sufficient bacterial mass containing reduced number of hybrid-plasmid-deleted cells and thereafter to produce the sufficient quantities of the foreign gene product by separating the period of the bacterial growth process from that of the foreign gene expression process to regulate the foreign gene expression by the above regulation of culture temperature in these two periods.

One objective of the present invention is to provide a simple and effective method of controlling expression of a desired foreign gene inserted into a hybrid plasmid in the culture of *E. coli* carrying the hybrid plasmid introduced therein.

Another objective of the present invention is to provide an appropriate method of effectively producing a desired foreign gene product in high concentration in the culture, particularly, for producing a foreign gene product on an industrial scale by using E. coil carrying a hybrid plasmid with an insertion of the foreign gene therein.

A method of regulating expression according to the present invention to achieve the above-mentioned objectives comprises a process of maintaining the temperature of culturing E. coli at or over 40° C. so as to suppress expression of a desired foreign gene in E. coil which carries the hybrid plasmid having been constructed by insertion of the desired foreign gene into an expression vector.

Thus, in a method of controlling expression according to the present invention, the expression of a foreign gene in a hybrid plasmid introduced into E. coli is effectively controlled by such a simple means as to control the culture temperature.

Furthermore, in applying a method according to the present invention to the production of a foreign gene product, sufficient bacterial cell growth and, at the same time, low incidence of the deletion of the hybrid plasmid from the bacterium can be achieved by distinctly separating the period of the cell growth process from that of the foreign gene expression process to efficiently proceed with those processes. As a result, by using this method, the product corresponding to the desired foreign gene is produced in the culture in high concentration so that efficient production of the foreign gene product can be achieved.

In accordance with the present invention, there is no need to use expensive inducers as required in the conventional method by using inducible-type plasmids, since the control of the expression of the foreign gene can be accomplished by such a simple method as manipulating the culture temperatures.

Furthermore, according to the present invention, the industrial scale mass culture for producing a foreign gene product can be easily facilitated because the incidence of hybrid-plasmid-deleted bacteria can be effectively suppressed.

BRIEF DESCRIPTION OF THE DRAWINGS

FIG. 2, consisting of (A)-(D), illustrates the nucleotide sequence of DNA including the regions encoding for PAL, the DNA having been cloned as described in Reference Example 1.

FIGS. 5-7 illustrate detailed partial views of the flowchart shown in FIG. 4.

FIGS. 12, 13, 14 and 15 are diagrams showing the culture conditions used tn Example 1, Example 2, Comparative Example 1 and Comparative Example 2, respectively.

DETAILED DESCRIPTION OF THE INVENTION

Figure 1:
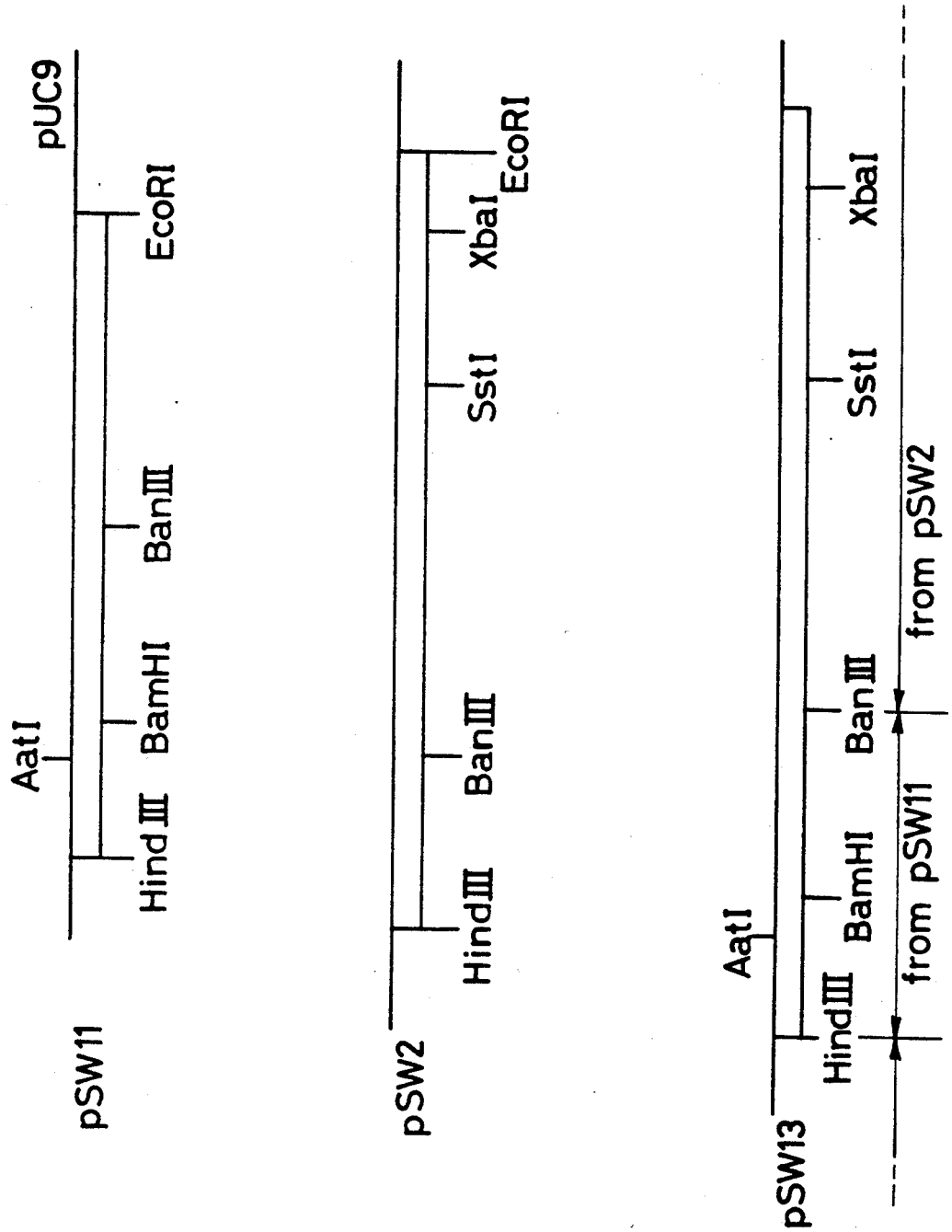
FIG. 1 illustrates restriction enzyme cleavage maps of the regions related to the structural gene for phenylalanine ammonialyase (PAL) in pSW11, pSW2 and pSW13.

A hybrid plasmid (recombinant plasmid) as used in the present invention is that obtained by insertion of a desired foreign gene into an expression vector which has a construction to permit expression of the foreign gene in E. coli.

An example of the expression vector consisting the hybrid plasmid comprises a vector which can replicate in E. coli and a promoter linked to the vector, the promoter being selected from a varieties of promoters such as the P$_L$ promoter of the lambda phage (the p$_L$lambda promoter); the promoter of tryptophan operon (the trp promoter); and a combined promoter comprising the P$_L$lambda promoter and the tac promoter composed of the trp promoter minus 35 region and the lac UV-5 promoter minus 10 region.

An example of the foreign gene as used in the present invention is a structural gene encoding for a polypeptide which is not usually produced by a wild type strain of E. coli, such as a polypeptide of non-E. coli origin having substantially the same amino acid sequence as that derived from a eukaryotic cell.

A method of regulating expression according to the present invention comprises controlling the temperature for culturing E. coli carrying a hybrid plasmid incorporated therein so as to regulate expression of a foreign gene being inserted into the hybrid plasmid.

More specifically, in order to suppress expression of the foreign gene, the temperature for culturing E. coli carrying the hybrid plasmid therein is to be set at or above 40° C. whereas the culture temperature is to be set below 40° C. to allow the foreign gene to be highly expressed.

When a bacterium carrying an incorporated hybrid plasmid therein is cultured at a temperature maintained at or above 40° C., the expression of a foreign gene in the hybrid plasmid can be effectively suppressed and the bacterium grows well and furthermore, incidence of hybrid-plasmid-deleted bacteria in the culture is effectively suppressed during the culture to obtain a desired number of cells.

In addition, a method according to the present invention permits controlling the expression of a foreign gene by such a simple means as to control the culture temperature so that there is no need to use specifically expensive reagents such as expression inducers as described above.

A foreign gene product derived from the foreign gene can be efficiently produced by using a method of the present invention in which E. coli carrying a hybrid plasmid with an insertion of the foreign gene therein is cultured under the specified conditions, thereby controlling the gene expression so as to effectively produce the foreign gene product.

More specifically, a method of regulating expression according to the present invention for producing a foreign gene product in E. coli carrying an incorporated hybrid plasmid therein comprises:

a) a first culture process in which E. coli carrying the hybrid plasmid incorporated therein is cultured at a temperature maintained at or above 40° C. and b) a second-culture process in which E. coli grown in the first culture process is cultured at a temperature below 40° C.

In the first culture process according to the present invention, the culture temperature is maintained at or above 40° C. so as to suppress the expression of the foreign gene which is present in the hybrid plasmid having been incorporated into E. coli. In consequence, E. coli grows sufficiently to give a desired number of cells in the culture of the first culture process. Furthermore, the incidence of the hybrid-plasmid-deleted cells is suppressed to the extent almost negligible during the period of cell growth. Furthermore, in the case of subculture for maintaining cell activity over a long period of time, the incidence of the hybrid-plasmid-deleted cells can be similarly suppressed by the method of thus controlling the foreign gene expression.

In the second culture process according to the present invention, the culture temperature is set below 40° C. so as to release the suppression of the foreign gene expression in the bacterial cell carrying the hybrid plasmid therein. Consequently, the foreign gene is highly expressed in the cell carrying the hybrid plasmid, thereby permitting the production of the foreign gene product. In this process, the number of hybrid-plasmid-deleted cells is almost negligible among the cells having been obtained during the first culture process so that the foreign genes in almost all the cells in the culture are to be expressed efficiently, thereby permitting the production of the foreign gene product in sufficiently high concentration.

An example of the ranges of the culture temperatures to be used in combination is 40°–45° C. for the first culture process and 25°–35° C. for the second culture process.

According to the present invention thus described, the yield of the foreign gene product can be geometrically increased since the foreign gene product is produced in high concentration when a large number of cells are cultured to obtain mass culture.

Furthermore, a method according to the present invention is applicable to the culture of prolonged period of time as required in the first culture process, whereas the aforementioned conventional method, in which cell growth is associated with the foreign gene expression, is not applicable to the culture of prolonged period because the rate of the hybrid-plasmid-deleted cells increases with prolongation of subculture time. Accordingly, a method according to the present invention is specifically suitable for the industrial mass culture where relatively long culture time is required for the preliminary culture.

The time to switch from the first culture process to the second culture process can be voluntarily selected as desired. However, it may depend on the kind of bacterium carrying the hybrid plasmid therein or on the culture method to be used for these culture processes. For example, when a method of the present invention is to be applied in the preliminary culture to obtain a small number of seed bacteria followed by the batch system mass culture to obtain the main culture, the first culture process may be adopted in the preliminary culture and for the first half of log phase of the main culture, and then the second culture process may be adopted in the culture thereafter.

A method according to the present invention will be more specifically understood from the following Reference Examples, Examples and Comparative Examples with the use of phenylalanine ammonialyase (hereinafter referred to as PAL).

REFERENCE EXAMPLE 1

(1) Isolation and purification of mRNA for PAL.

*Rhodosporidium toruloides* IFO 559 (also identified as ATCC. 10788) was grown at 27° C. under aerated and agitated conditions in a synthetic medium (Table I) containing 2% glucose. Immediately after depletion of the glucose in the culture, the cells were collected by centrifugation. The cells were washed with a sterile 0.85% sodium chloride solution and collected again by centrifugation to obtain washed wet cells.

TABLE 1

| | grams/l | | micrograms/l |
|---|---|---|---|
| Glucose | 20 | Biotin | 2 |
| $(NH_4)_2SO_4$ | 3 | Calcium pantothenate | 400 |
| $KH_2PO_4$ | 1 | Inositol | 2000 |
| $MgSO_4.7H_2O$ | 0.5 | Niacin | 400 |
| NaCl | 0.1 | p-Aminobenzoic acid | 200 |
| $CaCl_2$ | 0.1 | Pyridoxine hydrochloride | 400 |
| | | Riboflavin | 200 |
| | | Thiamine hydrochloride | 400 |

These washed wet cells were readily suspended in a PAL induction medium [i.e., 0.17% Yeast Nitrogen Base w/o Amino Acid and Ammonium Sulfate (Difco Laboratories) supplemented with 2% L-phenylalanine] to give a cell concentration of 0.5–0.8%, and the resultant suspension was incubated for the induction of PAL at 27° C. for 2 hours with shaking. After the induction, the cells were recovered by centrifugation. The collected wet cells were suspended in an equal volume of sterile water, and the resultant suspension was dropped into liquid nitrogen to obtain frozen cells.

Ten grams of the frozen cells having been treated for the PAL induction for 2 hours as described above was added to liquid nitrogen in a mortar and finely ground with a pestle. The liquid nitrogen evaporated spontaneously. As soon as the frozen ground material began to thaw, 50 ml of buffer solution "C" [composed of 0.1 M $Na_2HPO_4$ (pH 7.4), 0.15 M sodium chloride, 1% sodium deoxycholate and 1% Triton X-100 (registered trademark, Rohm & Haas, USA)] supplemented with 5% sodium dodecylsulfate (SDS) were added thereto. The resultant mixture was gently stirred for 30 minutes for thorough mixing.

After completion of the mixing, 50 ml of a phenol-chloroform mixture (composed of phenol, chloroform and isoamyl alcohol in a volume ratio of 25:24:1) was added thereto and mixed therewith by stirring for 15 minutes.

The resultant mixture was centrifuged to recover the aqueous layer. To this aqueous layer was added 50 ml of the phenol-chloroform mixture, followed by stirring for 15 minutes. The resultant mixture was then centrifuged again to recover the aqueous layer. This extraction procedure with the phenol-chloroform mixture was repeated twice more.

To the finally obtained aqueous layer was added 5 M NaCl so as to give a final sodium chloride concentration of 0.2 M. Then, 2.5 volumes of cold ethanol was add thereto. The resultant mixture was stored at or below −20° C. to precipitate nucleic acid components.

The precipitate so formed was collected by centrifugation, washed with cold ethanol and then dried under reduced pressure.

The dry material thus obtained was dissolved in 10 ml of sterile water, and the resultant solution was heated at 65° C. for 5 minutes. Thereafter, a mRNA component was isolated according to the method of Maniatis using oligo-d(T) cellulose [Maniatis, T., et al., "Molecular Cloning" (1982)].

The mRNA component thus obtained was dissolved in a sample buffer solution (composed of 5 M urea, 1 mM EDTA and 0.05% bromophenol blue) and then heated at 65° C. for 2 minutes to destroy the higher-order structure of mRNA. Thereafter, using an 8 M urea-acrylamide slab gel (having an acrylamide concentration of 3% and containing 8 M urea), the mRNA component was electrophoresed at 100 volts for 1.5 hours in an electrophoresis buffer solution (composed of 89 mM Tris, 89 mM boric acid and 2 mM EDTA).

After completion of the electrophoresis, the acrylamide gel was treated with ethidium bromide and mRNA bands were visualized under ultraviolet light. A gel portion supposedly including mRNAs ranging from 2.0 to 3.0 kb in size was divided into three equal parts in the lengthwise direction, and gel segments of the three parts were cut out of the slab gel.

Each gel segment was sealed into a dialysis tube, which was immersed in an electrophoresis buffer solution having the aforesaid composition. Thus, mRNAs were electrically eluted from the gel segments.

To the liquid inside the individual dialysis tube was added the phenol-chloroform mixture for the extraction of mRNA. The extraction procedure was repeated two times. The aqueous layer thus obtained was further treated with ether to remove residual phenol. To this finally obtained aqueous layer were added a 1/10 volume of a 3 M aqueous solution of sodium acetate (pH 5.2) and then 2.5 volumes of cold ethanol. The mixture thus obtained from each of the gel segments was stored at $-20°$ C. to precipitate mRNA.

In order to test for the presence of the mRNA for PAL in the mRNA preparation extracted from each of the three gel segment, mRNA in the preparation was translated into proteins and the proteins thus produced were tested with an antibody specific to PAL.

More specifically, individual mRNA was subjected to the translation with a cell-free translation kit using the lysate of rabbit reticulocytes [Pelham, H. R., et al., European J. Biochem., 67, 247–256 (1976)].

The rabbit reticulocyte assay kit used was a product of Promega Biotec Co. and the labeled amino acid used was $^{35}$S-methionine (Amersham Co.).

Identification of PAL in the proteins synthesized vitro was carried out by the translation of the mRNA in the rabbit reticulocyte translation system as follows:

To dissolve the proteins having been produced by the translation, buffer solution "C" was added to the translation reaction mixture. After removal of insoluble substances by centrifugation, anti-PAL rabbit (laboratory-made) was added to the reaction mixture. The reaction mixture was then allowed to stand on ice for 30 minutes. Subsequently, anti-rabbit IgG sheep serum (laboratory-made) was added to the reaction mixture. The mixture was allowed to stand on ice for 30 minutes to precipitate proteins together with the rabbit antibody component. The precipitate was recovered by centrifugation, washed twice with buffer solution "C" and then dissolved in a combined solution of a mixed solution of 2% SDS and beta-mercaptoethanol with another mixed solution of 0.1 M Tris-phosphate (pH 6.8), 1% SDS and 50% glycerol, in a volume ratio of 3:1. The resultant reaction mixture was heated at 95° C. for 2 hours to cleave disulfide bridges in the protein molecules. The solution was then subjected to SDS-polyacrylamide slab gel electrophoresis (at an acrylamide concentration of 10%) according to the method of Laemmli [Laemmli, U. K., Nature, 227 680–685 (1970)]. After completion of the electrophoresis, the gel was dried and the presence of PAL was detected by autoradiography.

Each of the mRNA fractions derived from the gel fragments was tested according to the procedure described above. Thus, the fraction containing the mRNA coding for PAL was identified.

(2) Synthesis of double-stranded cDNA (ds-cDNA) for PAL by using mRNA for PAL

The mRNA coding for PAL was purified from the gel segment obtained after electrophoresis of the mRNA fractions derived from the cells having been subjected to the treatment for the PAL induction for 2 hours as described above in Section (1). The mRNA thus obtained was treated with AMV reverse transcriptase for the synthesis of the single-stranded cDNA-transcript molecule of the mRNA for PAL [Gugger, U., et al., Gene, 25, 263–269 (1983)].

More specifically, cDNA-mRNA hybrid was first synthesized, consequently, mRNA was removed by treatment with RNase H and then the double-stranded cDNA (ds-cDNA) was constructed by treatment with DNA polymerase I and T4 DNA ligase.

(3) Construction of ds-cDNA having oligo-dC tails at 3'-termini

The ds-cDNA obtained in Section (2) above was treated with terminal deoxynucleotidyltransferase (TdT) to add oligo-dC tails to 3'-termini of the ds-cDNA.

More specifically, 3 micrograms of the ds-cDNA was dissolved in a TdT reaction buffer solution [composed of 100 mM potassium cacodylate (pH 7.2), 2 mM cobalt chloride and 0.2 mM dithiothreitol and supplemented with 0.2 mN dCTP]. After preheating of the buffer solution at 37° C. for 5 minutes, 50 units of TdT was added and the resultant reaction mixture was incubated at 37° C. for 15 minutes so as to allow the reaction to proceed. Thereafter, EDTA was added to a final concentration of 40 mM, subsequently the reaction mixture was placed on ice and the phenol-chloroform mixture was added to the reaction mixture to denature and inactivate the TdT. The reaction mixture was centrifuged to remove denatured insoluble proteins therein and the supernatant thus obtained was subjected to a phenol extraction. The aqueous layer was taken and mixed with cold ethanol. The precipitate so formed was collected, washed with 70% ethanol, and then dried under reduced pressure to obtain the ds-cDNA having oligo-dC tails at the 3'-termini.

(4) Construction of hybrid plasmid (Joint of plasmid pUC9 having oligo-dG tails to ds-cDNA having oligo-dC. tails)

The ds-cDNA with oligo-dC. tails obtained in Section (3) was joined to the plasmid pUC9 with oligo-dG tails (readily available from Pharmacia Co., Sweden) according to the method of Maniatis, known as the dC-dG homopolymer method.

(5) Transformation and clone selection

The hybrid plasmid obtained in Section (4) above, consisting of the oligo-dG tailed pUC9 and the oligo-dC tailed ds-cDNA, was introduced into CaCl$_2$-treated

*Escherichia coli* (MC-1061) [Casadaban, M. T., et al., Method in Enzymology, Vol. 100, 293–308, Academic Press, New York (1983)] according to the competent cell method.

From about 40,000 colonies obtained in the manner described above, transformed cells were selected according to the colony hybridization method based on the procedure of Grunstein et al. [Grunstein, M., et al., Proc. Natl. Acad. Sci., USA., 72, 3961 (1971)].

The probe DNA used in the colony hybridization was the $^{32}$P-labeled single-stranded cDNA obtained in the same manner as described above in Section (2), except that alpha-$^{32}$P-dCTP was added to the reaction mixture in place of unlabeled dCTP.

From the positive colonies thus obtained, plasmids were extracted and purified. The plasmids were digested with various restriction endonucleases, and the resultant DNA fragments were analyzed by agarose gel electrophoresis.

(6) Construction of ds-cDNA containing complete structure gene coding for PAL.

Plasmids pSW2 and pSW11 were isolated from the transformants obtained in Section (5) above.

Moreover, as a result of the analysis carried out in Section (5) above by using various restriction endonucleases, it was found out that the complete cDNA having the full length corresponding to the mRNA for PAL could be constructed by combining pSW2 with pSW11. Thus, these two plasmids were individually extracted and purified from the transformants carrying them. The plasmid obtained from the cell carrying pSW2 was digested with the restriction endonuclease BanIII, and then with the restriction endonuclease HindIII. The resultant fragment mixture was fractionated by agarose gel electrophoresis. Thus, a DNA fragment having a size of 4.2 kb was recovered and purified by subjecting several times to the procedure comprising treatment with the phenol-chloroform mixture and precipitation with cold ethanol.

Separately, the plasmid obtained from the cell carrying the pSW11 was digested with the restriction endonucleases BanIII and HindIII. By subjecting the resultant fragment mixture to electrophoresis, a DNA fragment having a size of 0.8 kb was recovered and purified.

The 4.2 kb and 0.8 kb DNA fragments thus obtained were circularized by using T4 DNA ligase, and the resultant product was used to transform *E. coli* (JM83, ATCC 35607) [Messing, J. and Vieira, J., Gene, 19, 259–268 (1982)].

Figure 3:
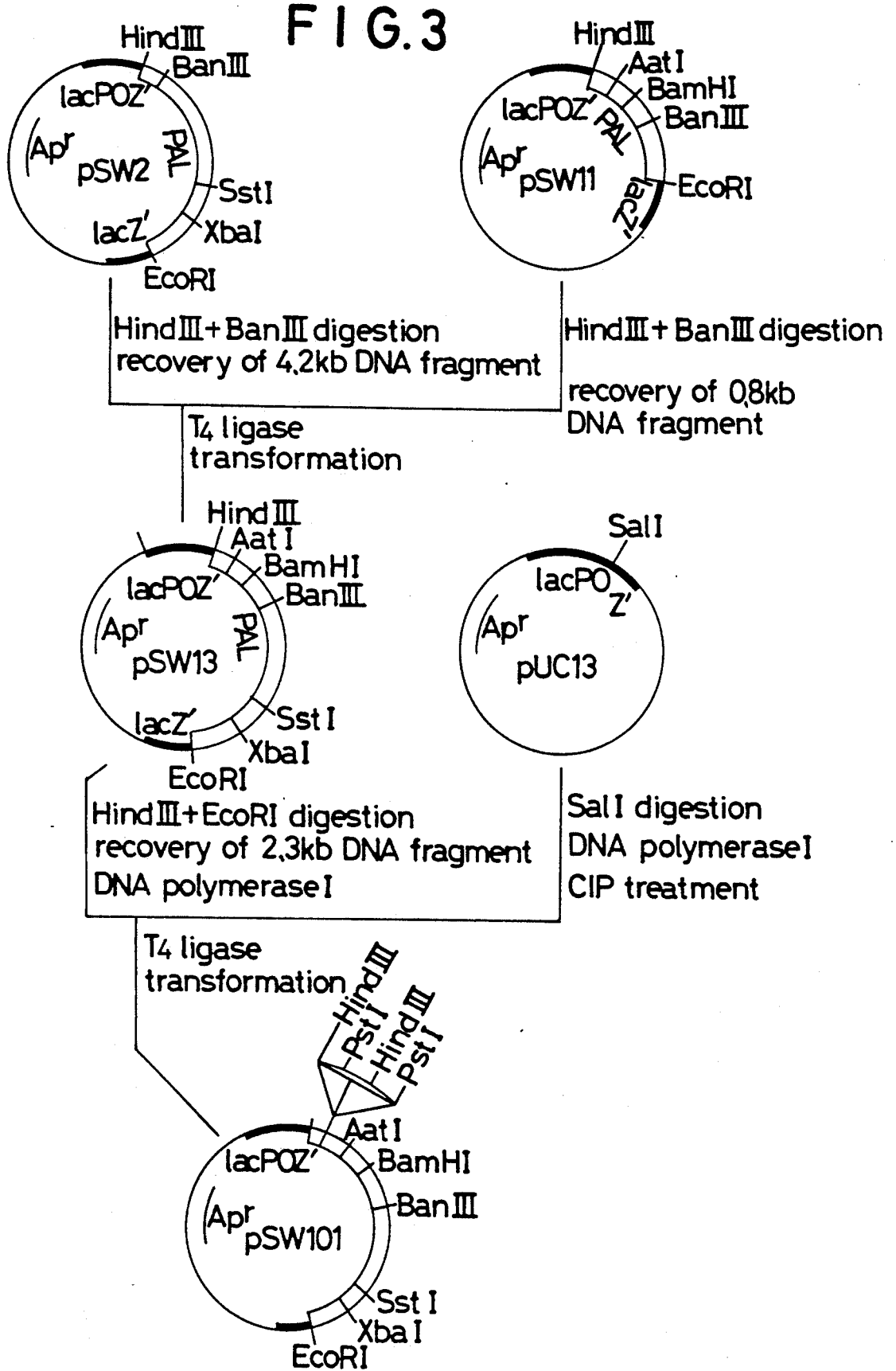
FIG. 3 is a flowchart showing the steps in process of constructing pSW101.

Plasmids extracted from the transformants having been selected by virtue of their ampicillin resistance were treated with various restriction endonucleases to construct cleavage maps. Thus, plasmid pSW13 containing the full length DNA structure for PAL was obtained. The restriction endonuclease cleavage map for DNA coding for PAL are shown in FIGS. 1 and 3.

(7) Determination of nucleotide sequence of cloned DNA

The cloned DNA from the plasmid pSW13 isolated from the cloned cell carrying the pSW13 was digested with various restriction endonucleases. Nucleotide sequences of the resultant restriction fragments were adequately analyzed by the method of Maxam-Gilbert (a chemical decomposition method) and also by biochemical means using the method of Maat (dideoxy method) [Maat, J., et al., Nuclei Acids Research, 5, 4537–4545 (1978)]. The nucleotide sequences thus obtained were edited by using the GENAS program produced by Mitsui Information Development Co. The DNA nucleotide sequence so determined is shown in FIG. 2, consisting of (A)–(D).

The structural gene coding for PAL including the initiator codon and the terminator codon comprises the nucleotide sequence extending from 1 to 2151.

(8) Construction of pSW101 (See FIG. 3)

In 14 microliters of a reaction medium [composed of 7 mM Tris-HCl (pH 7.5), 0.7 mM EDTA, 7 mM MgCl$_2$, 175 mM NaCl, 7 mM beta-mercaptoethanol and 0.01% bovine serum albumin (BSA), 0.9 micrograms of pUC13 (Pharmacia Co.) was digested with 10 units of the restriction endonuclease SaiI at 37° C. for 16 hours. After the digestion was accomplished, a linear pUC13 DNA fragment was obtained by the phenolchloroform treatment and ethanol precipitation.

Subsequently, the linear DNA was treated with the Klenow fragment of DNA polymerase I (Takara Shuzo K. K.) in a nick-translation buffer solution [composed of 50 mM Tris-HCl (pH 7.5), 10 mM MgCl$_2$, 0.1 mM dithiothreitol, 2% BSA, 80 μM dATP, 80 μM dGTP, 80 μM dTTP and 80 μM dCTP] at room temperature for 30 minutes. Thus, cohesive ends of the linear DNA were converted to flush ends. After the proteins were removed with phenol, the DNA fragment was recovered by precipitation with cold ethanol. Subsequently, in order to prevent self-circularization of the resultant linear pUC13 DNA, the 5'-terminal phosphoryl groups thereof were removed by treatment with phosphodiesterase from calf spleen (CIP; Boehringer Mannheim).

Separately, the plasmid pSW13 was extracted and purified from the clone carrying the pSW13. The plasmid pSW13 was treated with the restriction endonuclease DraI in a reaction medium [composed of 4 mM Tris-HCl (pH 7.5), 0.4 mM EDTA and 50 mM NaCl] at 37° C. for 28 hours. After the addition of a NaCl solution to the medium to give a sodium chloride concentration of 100 mM, the plasmid pSW13 was further treated with the restriction endonucleases EcoRI and HindIII at 37° C. for 16 hours.

After completion of the treatment, the reaction mixture was subjected to agarose gel electrophoresis, and a DNA fragment having a size of 2.3 kb was recovered from the gel. This DNA fragment was then subjected three times to the procedure comprising extraction with phenol, treatment with a phenol-chloroform mixture, and precipitation with cold ethanol. Thus, there was obtained a cDNA fragment coding for PAL.

In the aforesaid nick translation buffer solution, the cDNA fragment was treated with the Klenow fragment of DNA polymerase I at room temperature for 45 minutes, and then subjected three times to a procedure comprising treatment with a phenol-chloroform mixture and precipitation with cold ethanol. Thus there was obtained a cDNA fragment having flush ends.

The flush-ended cDNA thus obtained and the flush-ended pUC13 fragment prepared as above were joined by using T4 DNA ligase to construct the circular plasmid pSW101.

Using this hybrid plasmid, transformation of *E. coli* (JM83) was carried out according to the known method. Colonies were selected by virtue of ampicillin resistance and tested for the PAL activity. Consequently, the strain (MT-10410, FERM BP-8834) having the plasmid pSW101 was obtained.

(9) Construction of pYtrp6 and *E. coli* transformation thereby

The plasmid pSW101 constructed in the manner described above in Section (8) was digested with the restriction endonucleases PstI and BamHI. After electrophoresis on agarose gel, a fraction containing DNA of 370 bp was recovered. This fraction was divided into two portions and one was digested with BanI and the other with BbeI.

After the digestion, each fraction was subjected to acrylamide gel electrophoresis and thus a DNA fragment having a size of 70 bp from the digest with the BanI and a DNA fragment having a size of 280 bp from the digest with the BbeI were recovered.

The 70 bp fragment was treated with DNA polymerase I to obtain flush ends and then joined with ClaI (BanIII) linkers by means of ligation with T4 DNA ligase.

Figure 5:
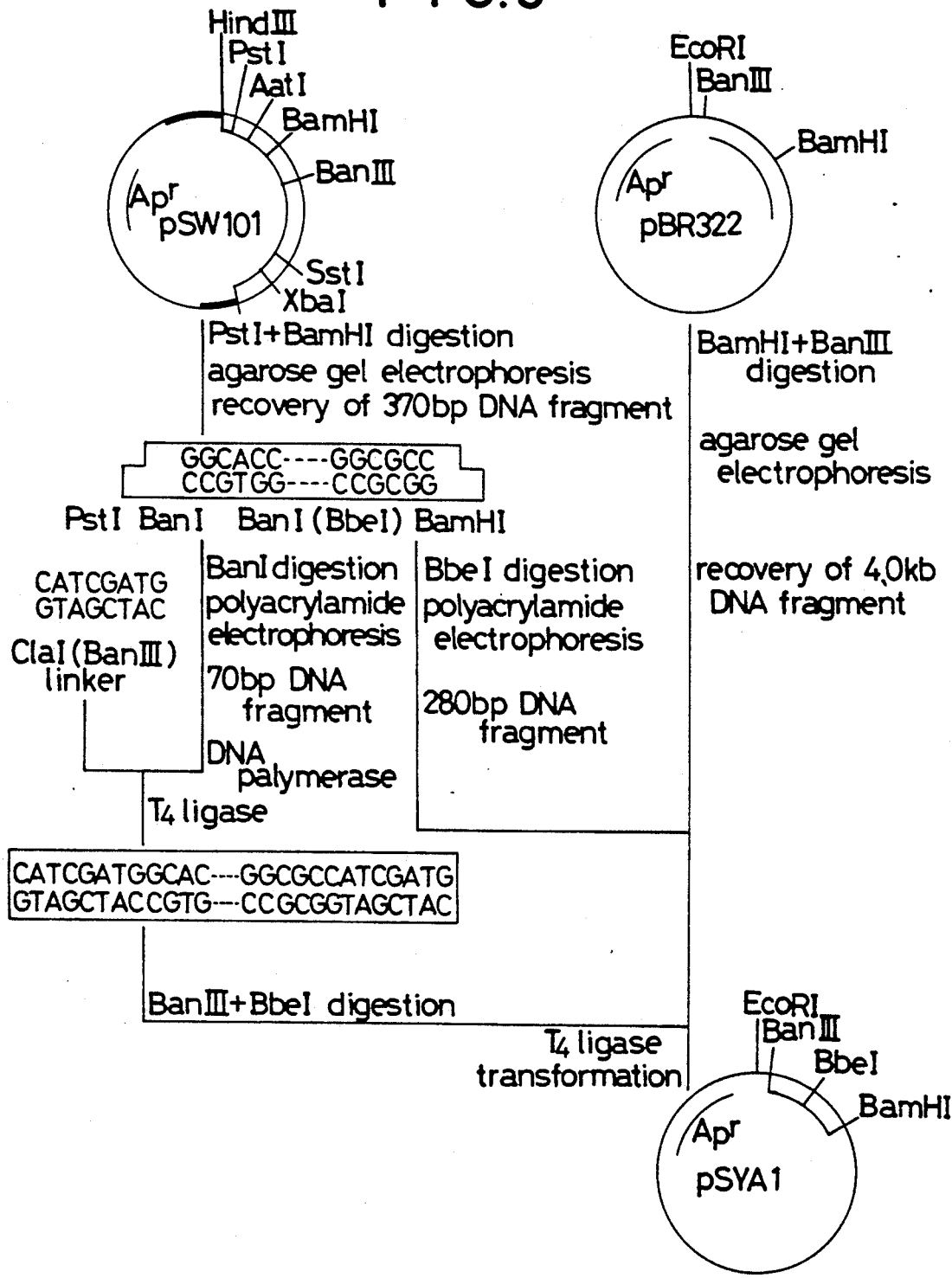

The resultant DNA fragment having ClaI linkers at both ends thereof was digested with the restriction endonucleases BanIII and BbeI. Subsequently, as illustrated in FIG. 5, the resultant DNA fragment including ClaI linkers and the previously prepared BbeI fragment (280 bp) were joined by using T4 DNA ligase to the 4.0 kb fragment having been obtained by digesting pBR322 (Pharmacia Co.) with the restriction endonucleases BanIII and BamHI. The plasmid pSYA1 was thus constructed. Further, with use of the plasmid pSYA1, transformation of *E. coli* (MC-1061) was curried out according to the conventional calcium method. The *E. coli* cells carrying the pSYA1 were grown at 37° C. overnight in 3 ml of ampicillin-supplemented LB medium [composed of 10 g of Bacto-Tryptone (registered trademark, Difco Laboratories), 5 g of Bacto-Yeast Extract (registered trademark, Difco Laboratories), 5 g of NaCl, 1 g of glucose and 1 l of distilled water, the pH adjusted to 7.5 with NaOH]. The cells collected by centrifugation were suspended in 60 microliters of a solution composed of 50 mM glucose, 25 mM Tris-HCl (pH 8.0) and 10 mM EDTA. Then, 40 microliters of a 10 mg/ml lysozyme solution was added thereto and the resultant mixture was allowed to stand at room temperature for 5 minutes. After completion of the reaction, 200 microliters of 0.2 N NaOH containing 1% SDS was added to the mixture. The reaction mixture was gently mixed by vortex, then placed on ice and allowed to stand thereon for 5 minutes. Then, 150 microliters of a 5 M sodium acetate solution (pH 4.8) was added to the mixture. After gentle mixing with vortex, the mixture was placed on ice to terminate the reaction.

The resultant cell lysate was centrifuged at 12,000 rpm for 10 minutes to separate supernatant. The supernatant was then subjected three times to a procedure comprising the treatment with the phenol-chloroform mixture and precipitation with cold ethanol.

From the precipitate thus obtained, plasmid pSYA1 was extracted according to the conventional method. The plasmid pSYA1 was digested with the restriction endonucleases BamHI and BanIII and then a DNA fragment having a size of 350 bp was recovered.

Separately, the plasmid pSW13 constructed in Section (6) above was digested with the endonuclease XbaI and the resultant cohesive ends were treated with DNA polymerase I to produce flush ends. Subsequently, the HindIII linkers were joined to the pSW13 by means of ligation with T4 DNA ligase to construct plasmid pSW13H. The plasmid pSW13H was then digested with the restriction endonucleases BamHI and HindIII and a DNA fragment having a size of 1.9 kb was recovered after agarose gel electrophoresis.

Separately, the plasmid pVV1 [Nicols, B. P., and Yanofsky, C., Method in Enzymology, 101, 155 (1983)] containing a part of the trp operon of *E. coli* was digested with the restriction endonuclease HinfI.

After agarose gel electrophoresis, a DNA fragment having a size of 0.9 kb was obtained from the gel according to the method described above.

Cohesive ends of the 0.9 kb DNA fragment having been produced by digestion with the HinfI were converted to flush ends according to the procedure described in Section (8) above. The EcoRI linkers (GGAATTCC) were then joined to the 5'-flush ends of the DNA fragment by ligation with T4 DNA ligase.

The DNA fragment having the EcoRI linkers thus prepared was treated with the restriction endonuclease EcoRI to produce a DNA fragment having EcoRI-cleaved cohesive ends [Nicols, B. P. and Yanofsky, C., Method in Enzymology, 101, 155 (1983)].

Using T4 DNA ligase, the DNA fragment having the EcoRI cohesive ends was joined to the DNA fragment which had been obtained by treating the EcoRI-digested pBR322 with CIP according to the procedure described above in Section (8). The resultant product was then digested with the restriction endonucleases EcoRI and BglII. The digest was then subjected to agarose gel electrophoresis to obtain a DNA fragment having a size of 0.4 kb.

This 0.4 kb DNA fragment having three cleavage sites for the restriction endonuclease TaqI was partially digested with TaqI. A DNA fragment having a size of 345 bp was thus obtained.

This 345 bp DNA fragment was joined to the 4.3 kb DNA fragment obtained by digesting pBR322 with the restriction endonuclease EcoRI and ClaI. Thus, plasmid pFtrp2 containing the trp promoter was obtained.

Figure 6:
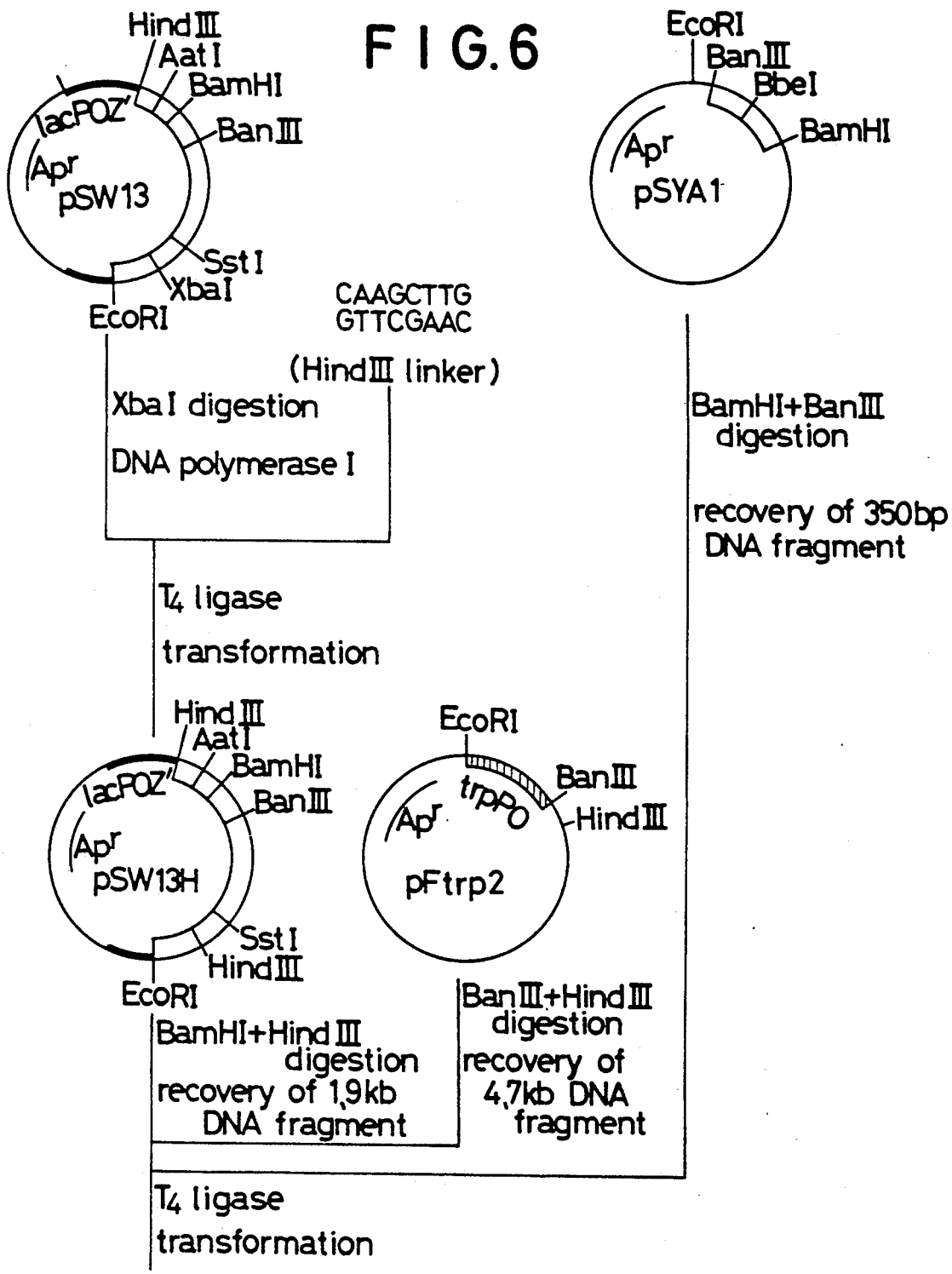

The plasmid pFtrp2 constructed in the manner as described above was digested with the restriction endonucleases BanIII and HindIII. After agarose gel electrophoresis, a fragment of 4.7 kb was obtained. As illustrated in FIG. 6, this fragment was then joined to the 350 bp BamHI-BanIII fragment and the 1.9 kb BamHI-HindIII fragment, both previously prepared, by ligation with T4 DNA ligase. The circular plasmid pSYA2 as shown in FIG. 7 was thus constructed.

Subsequently, the plasmid pSYA2 was partially digested with BanIII and the resultant cohesive ends thereof were treated with DNA polymerase I to produce a flush-ended fragment. This fragment was then circularized by ligation with T4 DNA ligase to construct plasmid pYtrp6 having a cleavage site for NruI (FIG. 7).

*E. coil* (MC-1061) was transformed with the plasmid pYtrp6 according to the conventional method. Cloned cells were selected by virtue of ampicillin resistance and were tested for the PAL activity. The transformed cell of *E. coil* exhibiting the PAL activity thus isolated was named MT-10414 (FERM Bp-1712).

Figure 4:
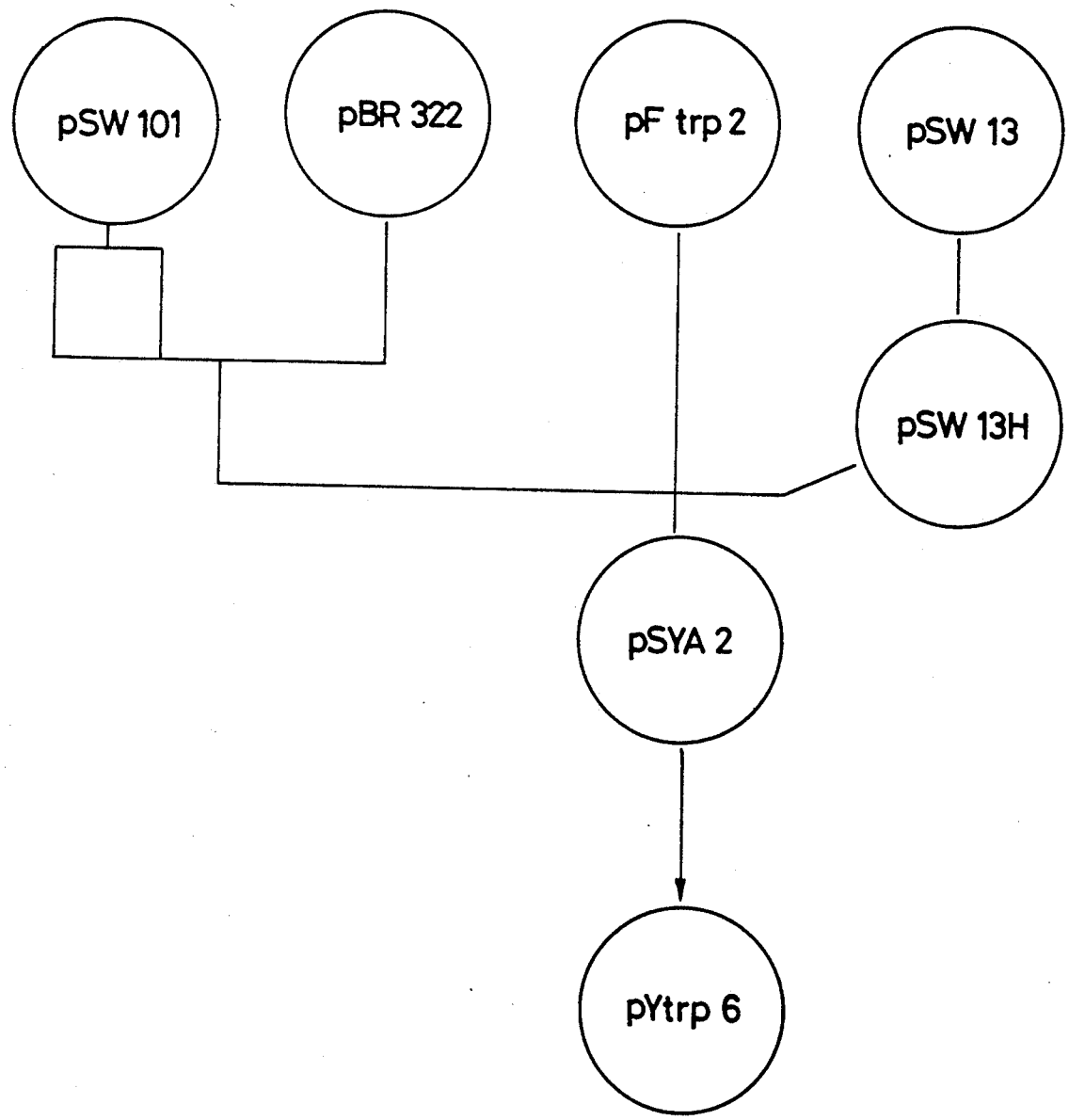
FIG. 4 is a flowchart showing the steps in process of constructing pYtrp6.

The steps of construction of the plasmid pYtrp6 is illustrated in outline in FIG. 4 and in detail in FIGS. 5, 6 and 7. Reference Example 2 (Construction of plasmid pSW115)

Figure 8:
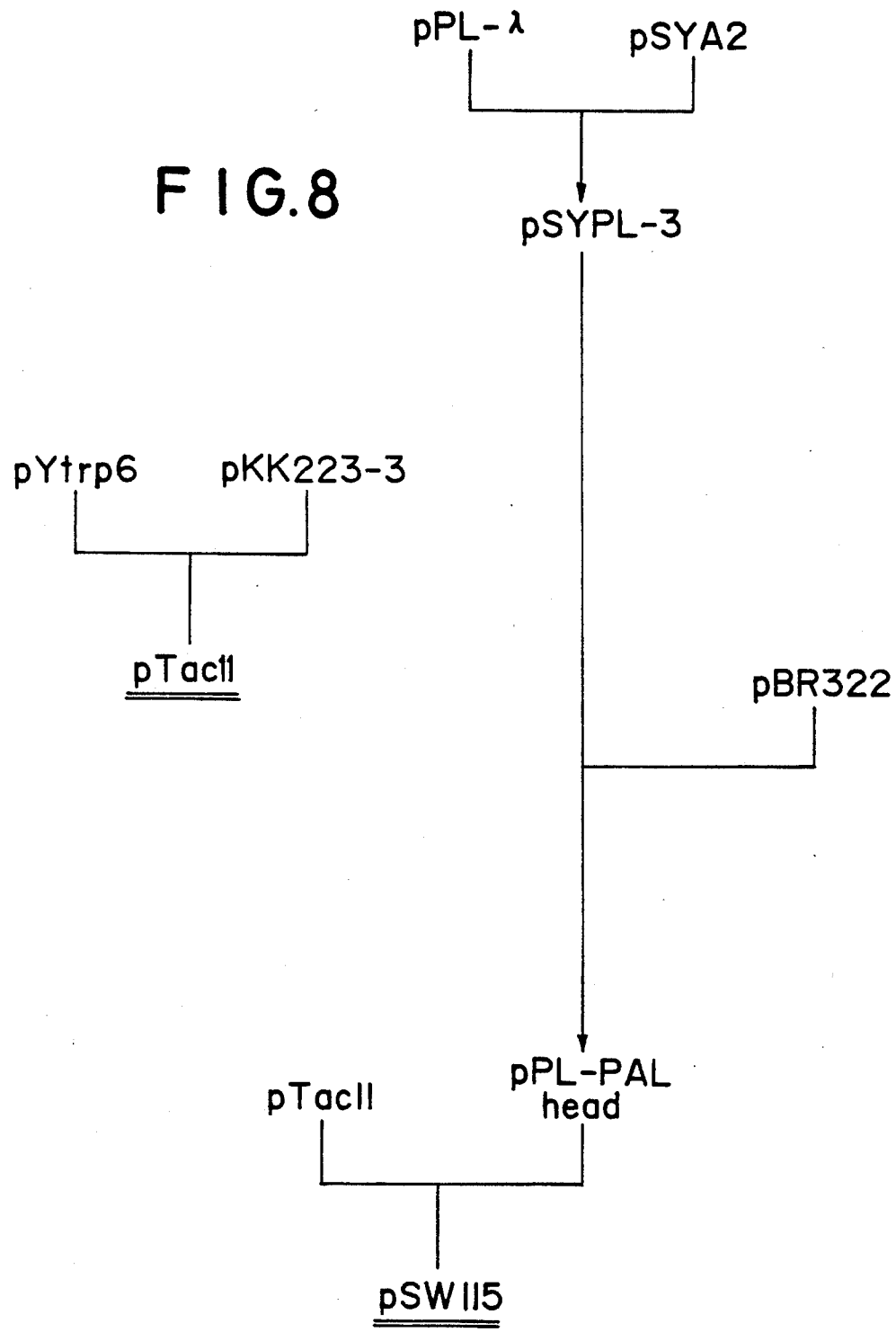
FIG. 8 illustrates schematic diagrams showing steps in process of constructing hybrid plasmids constructed in Reference Example 2.

The procedures for construction of various plasmids in Reference Example 2 are outlined in FIG. 8. (1)

Figure 9:
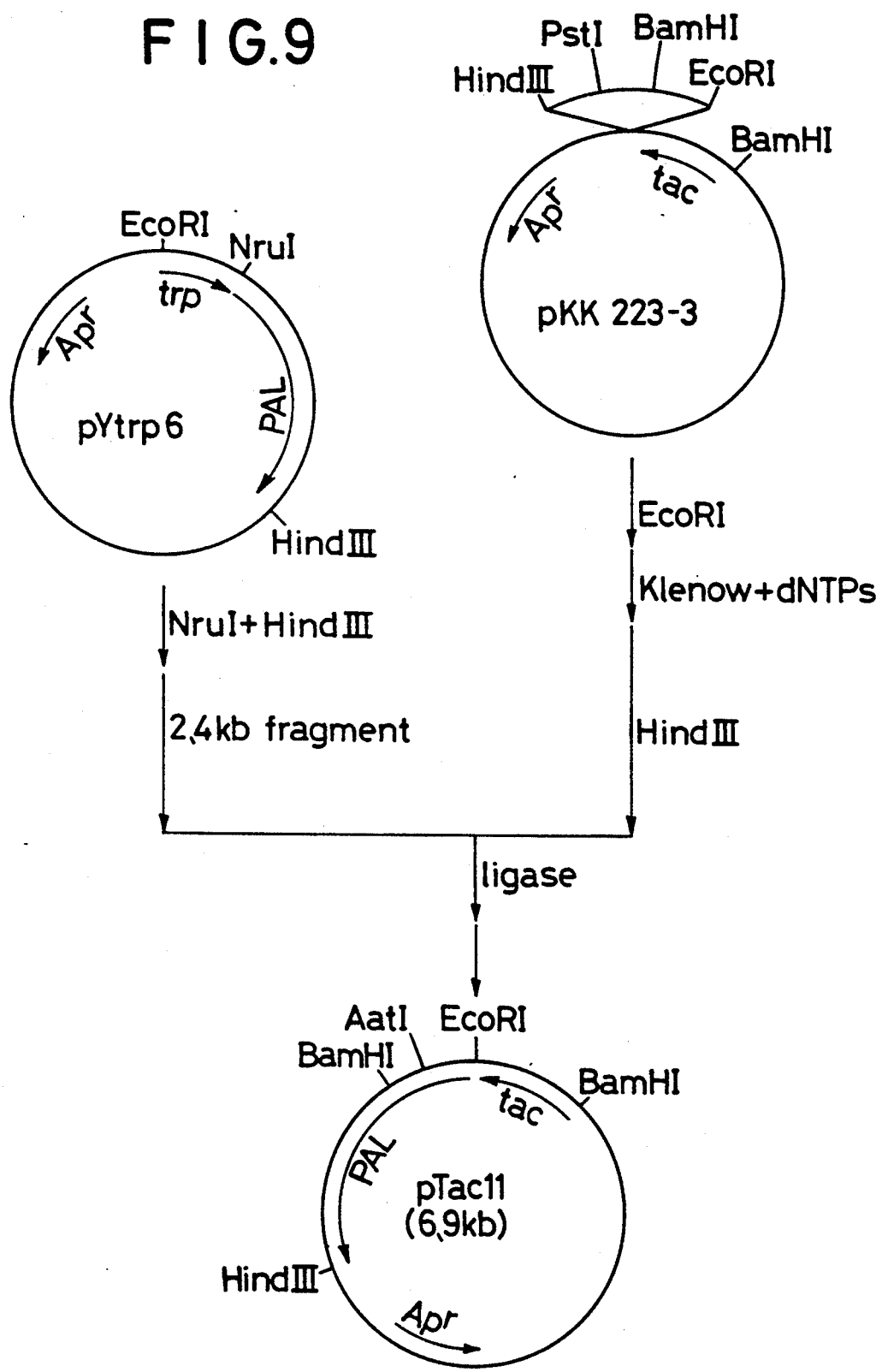
FIGS. 9, 10 and 11 illustrate detailed steps in process of constructing the hybrid plasmids pTac11, pP$_L$-PAL-head and pSW115, respectively.

Construction of plasmid pTac11 according to the procedure illustrated in FIG. 9.

Firstly, the plasmid pYtrp6 was extracted from the *E. coli* MT-10414 (FERM Bp-1712) carrying the pYtrp6 with an insertion therein of the structural gene for PAL obtained from *Rhodosporidium toruloides* according to the method described in Reference example 1. The plasmid thus obtained was digested with the restriction endonucleases NruI and HindIII. After electrophoresis, a DNA fragment having a size of 2.4 kb was obtained.

Separately, the plasmid pKK223-3 (Pharmacia Co.) carrying the tac promoter was digested with the restriction endonuclease EcoRI to obtain a DNA fragment having cohesive ends. The DNA fragment was then treated with DNA polymerase I to change the cohesive ends thereof to flush ends.

Thereafter, the flush-ended DNA fragment was digested with the restriction endonuclease HindIII to obtain a DNA fragment having cohesive ends. This DNA fragment was then ligated with the previously prepared 2.4 kb DNA fragment in the presence of T4 DNA ligase. The resultant product was introduced into *E. coil* (MC-1061) according to the method of Cohen et al. [Cohen, S. N., et al., Proc. Natl. Acad. Sci. USA, 69, 2110 (1982)].

Subsequently, the *E. coil* carrying the product introduced was grown on an ampicillin plate prepared by adding 1.5% agar to the aforementioned LB medium supplemented with ampicillin at a concentration of 50 micrograms/ml. After completion of the incubation, cloned cells were selected by virtue of ampicillin resistance and then plasmid molecules were extracted from the clones. The endonuclease cleavage map of the individual plasmid was constructed and consequently, the clone carrying the desired plasmid pTac11 having the structure illustrated in FIG. 9 was identified and the pTac11 was prepared from the cloned cells.

Figure 10:
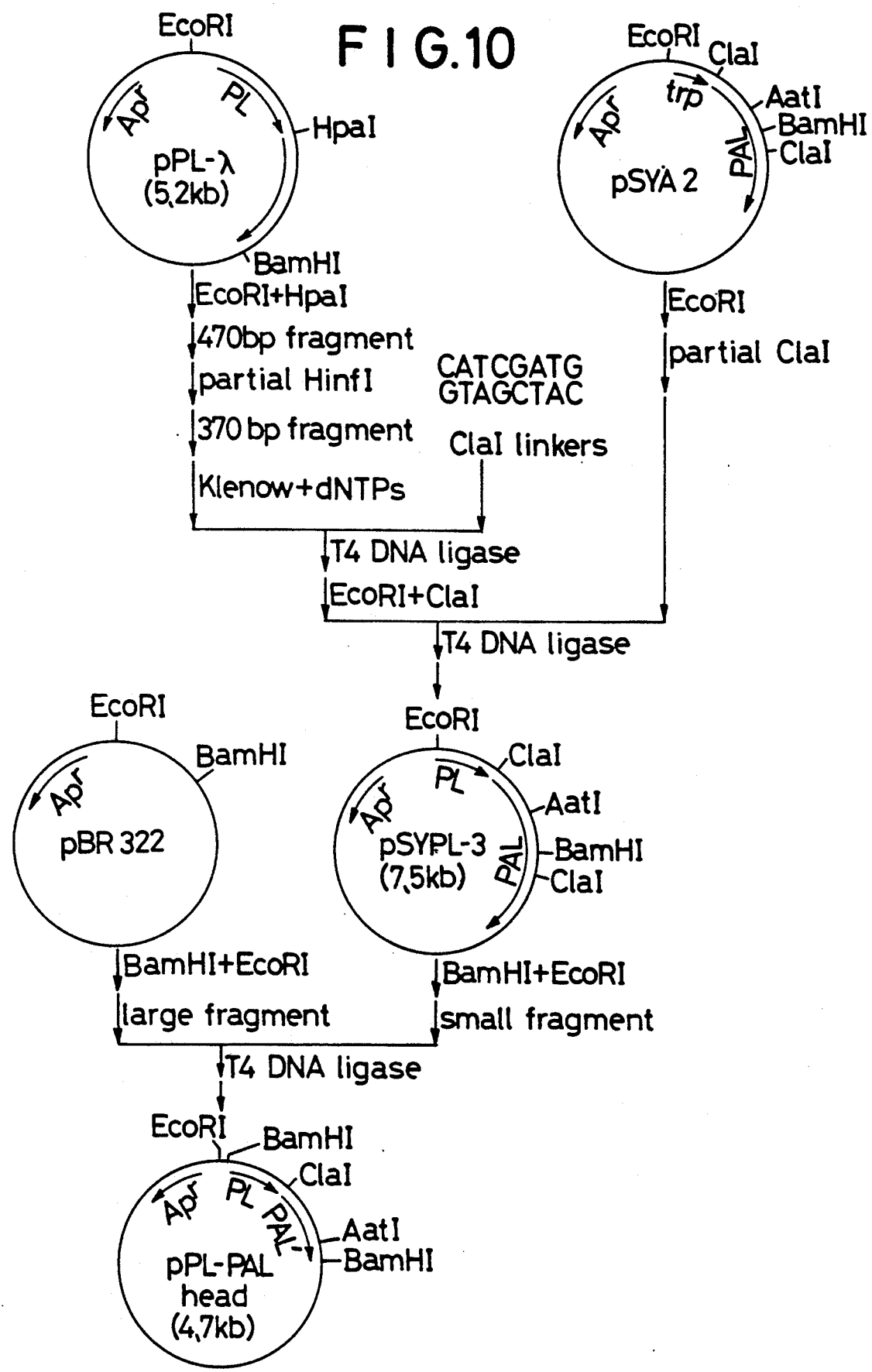

(2) Construction of plasmid $pP_L$-PAL-head according to the procedure illustrated in FIG. 10.

The plasmid $pP_L$-lambda (Pharmacia Co.) was digested with the restriction endonucleases EcoRI and HpaI. After electrophoresis, a DNA fragment of 470 bp was obtained. This 470 bp DNA fragment was partially digested with the restriction endonuclease HinfI. After electrophoresis, a DNA fragment of 370 bp was obtained.

Furthermore, the 370 bp DNA fragment was treated with DNA polymerase I to produce flush ends at 5'-termini thereof. The flush-ended DNA fragment thus prepared was allowed to react with ClaI linkers in the presence of T4 DNA ligase. After completion of the reaction, the resultant product was digested with the restriction endonucleases EcoRI and ClaI to obtain a fraction containing a mixture of large and small EcoRI-ClaI DNA fragments.

Separately, the plasmid pSYA2, which had been constructed in the process of cloning the structural gene for digested with the restriction endonuclease EcoRI. The resultant DNA fragment was further partially digested with the restriction endonuclease ClaI. After electrophoresis, a large DNA fragment was separately obtained from a mixture of large and small EcoRI-ClaI DNA fragments.

The large DNA fragment thus obtained from the plasmid pSYA2 was allowed to react in the presence of T4 DNA ligase with the previously prepared fraction containing the mixture of large and small EcoRI-ClaI fragments. The resultant reaction products were introduced into *E. coil* (MC-1061), and the *E. coli* cells were grown on an ampicillin plate. After completion of the incubation, colonies were selected by virtue of ampicillin resistance and then a plasmid molecule was extracted from the individual cloned cell. The endonuclease cleavage map of the individual plasmid molecule was constructed. Consequently, the clone carrying the desired plasmid $pSYP_L$-3 having the structure illustrated in FIG. 10 was identified and the plasmid $pSYP_L$-3 was prepared from the cells derived from this clone.

This clone was named MT-10424 (FERM BP-1714).

Furthermore, the plasmid $pSYP_L$-3 thus obtained was digested with the restriction endonucleases EcoRI and BamHI. After electrophoresis, a small DNA fragment was obtained from the resultant mixture of large and small EcoRI-BamHI fragments.

Separately, the plasmid pBR322 (Pharmacia Co.) was digested with the restriction endonucleases EcoRI and BamHI. A large DNA fragment was separately obtained from the resultant mixture of large and small EcoRI-BamHI DNA fragments after electrophoresis. The large DNA fragment thus obtained from the plasmid pBR322 was then allowed to react in the presence of T4 DNA ligase with the small fragment previously prepared from the plasmid $pSYP_L$-3. Consequently, plasmid $pP_L$-PAL-head having the structure illustrated in FIG. 10 was obtained. In order to confirm that the desired plasmid was obtained, the resultant product of the aforementioned reaction in the presence of T4 DNA ligase was introduced into *E. coli* (MC-1061) and then the *E. coil* cells were grown on an ampicillin plate. Cloned cells were selected by virtue of the ampicillin resistance and then a plasmid molecule was extracted from the clones. The endonuclease cleavage map of the individual plasmid was constructed to verify the presence of the desired plasmid.

Figure 11:
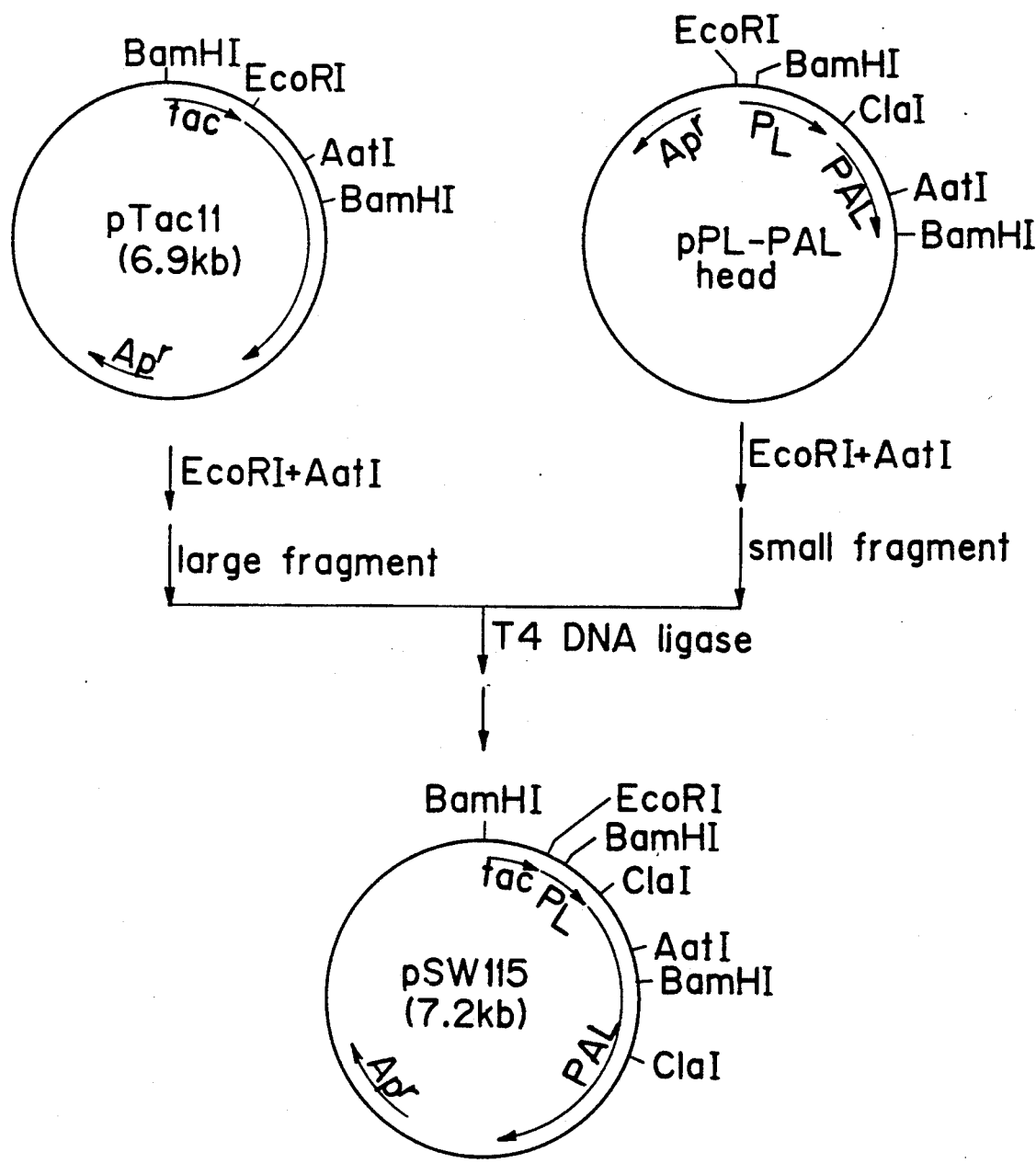

(3) Construction of plasmid pSW115 according to the procedure illustrated in FIG. 11.

Firstly, the plasmid pTac11 obtained in Section (1) above was digested with the restriction endonucleases EcoRI and AatI. After electrophoresis, a large DNA fragment was separately obtained from a mixture of large and small EcoRI-AatI DNA fragments.

Separately, the plasmid $pP_L$-PAL-head obtained in section (2) above was digested with the restriction endonucleases EcoRI and AatI. After electrophoresis, a small DNA fragment was separately obtained from a mixture of large and small EcoRI-AatI DNA fragments.

Finally, the aforementioned large DNA fragment derived from the plasmid pTac11 was joined to the aforementioned small DNA fragment derived from the plasmid $pP_L$-PAL-head by ligation with T4 DNA ligase. The plasmid pSW115 was thus obtained.

In order to confirm that the desired plasmid was to obtained, the plasmid produced by the aforementioned reaction was introduced into *E. coli* (MC-1061) and the resultant transformants were selected on an ampicillin plate. A plasmid molecule was extracted from the individual cloned cell and the endonuclease cleavage map of the plasmid molecule was constructed. At the same time, the transformant was tested for the PAL activity according to the procedure described hereinafter. The transformed strain of *E. coli* having the PAL activity thus obtained was named MT-10423 (FERM BP-1713).

(4) Expression of PAL by using plasmid pSW115

The transformed cell of *E. coli* carrying the plasmid pSW115 therein obtained in Section (3) above was inoculated into LB medium (pH 7.5) supplemented with ampicillin at a concentration of 50 micrograms/ml as aforementioned. The inoculated medium was incubated with shaking at 30° C. for 20 hours.

After completion of the incubation, the culture exhibited such a cell concentration as to give an optical density (O.D. at 660 hm) of 5.40. The cells were collected from the culture by centrifugation and then tested for the PAL activity according to the procedure described hereinafter. The specific activity of the cells thus obtained was 630 U/g cells (dry weight).

Determination of PAL activity

The PAL activity of the cell extract was determined as follows by using the enzymatic reaction in which cinnamic acid is synthesized from L-phenylalanine.

First, cells were recovered from the culture by centrifugation. The collected cells were washed by suspending them in a 0.85% sodium chloride solution and recovered by centrifugation. The washed cells were then suspended in a 25 mM Tris-HCl buffer solution (pH 8.8) to give a cell concentration of about 1% by wet weight. The suspension was added to an enzymatic reaction medium comprising a 25 mM Tris-HCl buffer solution (pH 8.8) supplemented with 25 mM L-phenylalanine and 0.005% cetyl pyridium hydrochloride. The resultant reaction medium was incubated at 30° C. for 20 minutes. After the reaction was terminated by addition of 1N HCl, cinnamic acid formed in the reaction mixture was analyzed by liquid chromatography to estimate the PAL activity. One unit (U) as defined herein corresponds to the amount of enzyme to produce one micromole of cinnamic acid per minute.

The amount of the cells used for the calculation was the dry weight of the corresponding washed cells.

In the above Reference Examples., the introduction of the recombinant plasmid in *E. coli* was carried out according to the method of Cohen et al. [Cohen, S. N., et al., Proc. Natl. Acad. Sci. USA, 69, 2110 (1982)]. Unless otherwise specified, plasmids or DNA fragments were treated with restriction endonucleases, T4 DNA ligase or DNA polymerase I in usual manners and the preparations of plasmids from bacterial cells were carried out in conventional manners and further the restriction endonucleases, linkers, T4 DNA ligase and DNA polymerase I used were products of Takara Shuzo K. K.

EXAMPLES AND COMPARATIVE EXAMPLES

The present invention will be explained by the following Examples and Comparative Examples.

Media hereinafter used in Examples and Comparative Examples were prepared as follows.

LB-AP medium

LB medium consisting of the following constituents was autoclaved at 120° C. for 15 minutes and was aseptically supplemented with ampicillin (AP) at a concentration of 50 micrograms/ml.

| LB medium component | |
|---|---|
| Tryptone | 10 g |
| Yeast extract | 5 g |
| Glucose | 1 g |
| NaCl | 5 g |
| Distilled water | 1 l |

(The pH of the medium was adjusted to 7.2 with KOH) LB agar medium:

LB medium consisting of the aforementioned constituents was supplemented with agar at a concentration of 15g/l and then autoclaved at 120° C. for 15 minutes. The resultant medium was dispensed into petri dishes to prepare LB-agar medium plates.

LB-AP agar medium

LB medium consisting of the aforementioned constituents was supplemented with agar at a concentration of 15 g/l and then autoclaved at 120° C. for 15 minutes. After autoclaving, the medium was aseptically supplemented with ampicillin at a concentration of 20 micrograms/ml and then dispensed into petri dishes to prepare LB-AP agar medium plates. Synthetic medium:

The following ingredients were dissolved into one liter of distilled water and the pH of the solution was adjusted to 7.2 with KOH.

| Polypeptone | 10 g |
|---|---|
| Yeast extract | 5 g |
| Dipotassium phosphate | 1 g |
| Magnesium sulfate.2H$_2$O | 0.5 g |

EXAMPLE 1

The culture of *E. coli* MT-10423 (FERN BP-1713) carrying the hybrid plasmid pSW115 introduced therein was spread on an LB-AP agar medium plate and incubated at 37° C. The hybrid plasmid pSW115, having been constructed in the course of Reference Example 2, comprises the expression vector carrying the gene encoding for ampicillin resistance with the insertions of the combined promoter comprising the tac promoter and the P$_L$lambda promoter linking at the downstream of the tac promoter and the PAL structural gene being inserted at the downstream of the combined promoter.

A portion of the bacterial cells taken from the colony appearing on the plate was transferred as an inoculum into LB-AP medium (5 ml) in a test tube equipped with a cotton plug. The tube was incubated at 42° C. for 12 hours with shaking at 110 strokes/min. After the incubation, an aliquot of 15 microliters each of the culture (including cultured cells) was taken up as an inoculum into fresh LB-AP medium (5 ml each) in two cotton-plug-equipped test tubes. The tubes were incubated with shaking at the same rate as described above at 41° C. for the one tube and at 30° C. for the other tube to obtain two culture fluids designated as culture No. 1-1 (incubated at 41° C. for 12 hours) and culture No. 1-2 (incubated at 30° C. for 20 hours).

Fifteen microliters each of the culture fluid (including cultured cells) of culture No. 1—1 was taken up as an inoculum into fresh LB-AP medium (5 ml each) in two cotton-plug-equipped test tubes. The tubes were then incubated with shaking as described above at 42° C. for the one tube and at 30° C. for the other tube to obtain two culture fluids; culture No. 1-3 (incubated at 42° C. for 12 hours) and culture No. 1-4 (incubated at 30° C. for 20 hours). Incubation was further continued under the conditions as described above, except that the incubation temperature and time were set as shown in FIG. 12. Thus, cultures No. 1-5, No. 1-6, and No. 1-7 were obtained.

Cultures No. 1-2, No. 1-4, No. 1-6 and No. 1-7 were centrifuged immediately after the incubation to collect cells. The cells were suspended and washed in a 0.85% NaCl aqueous solution and then collected again by centrifugation. The cells thus recovered were frozen for storage.

Subsequently, the frozen cells of each culture were defrosted to prepare the cell extract for determination of the PAL specific activity in the manner as hereinafter described. The results are shown in Table 2.

Preparation of cell extract

The frozen cells were suspended in a 0.05 M Tris-HCl buffer solution (pH 8.8) at a cell concentration of 2% by wet weight and was subjected to ultrasonic treatment to destruct the cells. Resultant cell debris in the suspension was removed by centrifugation to prepare the cell extract.

Determination of PAL activity

The PAL activity of the cell extract was determined as follows by using the enzymatic reaction in which cinnamic acid is synthesized from L-phenylalanine.

First, a sample of a cell extract was diluted with a 25 mM Tris-HCl buffer solution (pH 8.8) to give a cell concentration of about 1% by wet weight and a 1.0 ml portion thereof was added to 4.0 ml of a 31.25 mM Tris-HCl buffer solution (pH 8.8) supplemented with 31.25 mM L-phenylalanine. The resultant solution was allowed to react at 30° C. for 20 minutes and then the reaction was terminated by the addition of 1 ml of 1N-HCl. The amount of cinnamic acid produced in the reaction mixture was determined by liquid chromatography under the conditions as hereinafter described to estimate the PAL activity.

One unit (U) as defined herein is the amount of the enzyme to produce one micromole of cinnamic acid per minute.

Conditions for liquid chromatography

An isolation column, YMC Pack A-312 (Yamamura Chemical Laboratories, Japan), was used with a mobile phase of methanol:water:phosphoric acid (50:41:0.08 v/v) and cinnamic acid was detected with an ultraviolet spectrophotometer at the detection wave length of 260 nm.

The amount of the cells used for the calculation of the PAL specific activity was the dry weight of the corresponding washed cells.

COMPARATIVE EXAMPLE 1

Cultures No. 2-1, No. 2-2, No. 2-3, No. 2-4, No. 2-5, No. 2-6 and No. 2-7 were obtained in the same manner as described in Example 1, except that the incubation temperatures of 40° C. and over used in Example 1 were alternatively changed to the temperatures indicated in FIG. 13.

Further, frozen stock Cells were prepared from the cultures No. 2-2, No. 2-4, No. 2-6 and No. 2-7 tn the same manner as described in Example i and the PAL specific activity of each cell extract was determined. The results are shown in Table 2.

TABLE 2

|  | Example 1 | | | | Comparative Example 1 | | | |
|---|---|---|---|---|---|---|---|---|
| Frequency of subculture | 0 | 1 | 2 | 3 | 0 | 1 | 2 | 3 |
| Culture No. | 1-2 | 1-4 | 1-6 | 1-7 | 2-2 | 2-4 | 2-6 | 2-7 |
| Incubation temperature, °C. | 42 | 41 | 42 | 43 | 36 | 38 | 37 | 37 |
| PAL specific activity of cells cultured at 30° C. (U/g cells*) | 303 | 341 | 345 | 337 | 303 | 380 | 132 | 53 |

*Dry weight.

EXAMPLE 2

The culture of E. coli carrying a hybrid plasmid introduced therein was spread on an LB-AP agar medium plate and finally, serial incubations were curried out to obtain culture fluids in the same manner as described in Example 1, except that in place of E. coil MT-10423, E. coli MT-10424 (FERM BP-1714) carrying the hybrid plasmid pSYP$_L$-3 therein was used and that the incubations were carried out at the temperatures indicated in FIG. 14. The hybrid plasmid pSYP$_L$-3, having been constructed in the course of Reference Example 2, comprises the expression vector carrying the gene encoding for ampicillin resistance with the insertions of the P$_L$lambda promoter/operator and the PAL structural gene being inserted at the downstream of the P$_L$lambda promoter/operator region.

Cultures No. 3-1, No. 3-2, No. 3-3, No. 3-4, No. 3-5, No. 3-6 and No. 3-7 were thus obtained.

Further, as described in Example 1, frozen cells were prepared from the cultures No. 3-2, No. 3-4, No. 3-6 and No 3-7 and the PAL specific activity of each cell extract was determined. The results are shown in Table 3.

COMPARATIVE EXAMPLE 2

Culture fluids were obtained in the same manner as described in Comparative Example 1, except that E. coli MT-10424 having the hybrid plasmid pSYP$_L$-3 as used in Example 2 was used in place of E. coil MT-10423 and that the incubations were carried out at the temperatures as indicated in FIG. 15. Cultures No. 4-1, No. 4-2, No. 4-3, No. 4-4, No. 4-5, No. 4-6 and No. 4-7 were thus obtained.

Furthermore, in the same manner as described in Example 1, frozen cells were prepared from the cultures No. 4-2, No. 4-4, No. 4-6 and No. 4-7 and the PAL specific activity of each cell extract was determined. The results are shown in Table 3.

TABLE 3

|  | Example 2 | | | | Comparative Example 2 | | | |
|---|---|---|---|---|---|---|---|---|
| Frequency of subculture | 0 | 1 | 2 | 3 | 0 | 1 | 2 | 3 |
| Culture No. | 3-2 | 3-4 | 3-6 | 3-7 | 4-2 | 4-4 | 4-6 | 4-7 |
| Incubation temperature, °C. | 42 | 42 | 41 | 42 | 35 | 34 | 35 | 35 |
| PAL specific activity of cells incubated at 30° C. (U/g cells*) | 250 | 248 | 252 | 250 | 245 | 197 | 120 | 50 |

*Dry weight.

As is evident from the results in Tables 2 and 3, no decrease in the PAL specific activity during subcultures was observed in the extracts of the cells cultured at 30° C. in the cases of Examples 1 and 2 in which the subcultures were curried out at the temperatures of 40° C. or over. In other words, in the cultures obtained through the stages of the first and second culture processes according to the present invention, there was no decrease in the PAL specific activity even after the frequent subcultures.

In contrast, with increased frequency of the subcultures, a remarkable decrease in the PAL specific activity was observed in the extracts of the cells cultured at 30° C. in the cases of comparative Examples 1 and 2 in which the subcultures were curried out at the temperatures below 40° C.

Furthermore, the cultures obtained in the aforementioned Examples and Comparative Examples were spread on LB-AP agar medium plates and LB agar medium plates each in an equal amount. After incubation at 37° C., numbers of colonies appeared on the paired plates for the each cultures were compared so as to find the rate of the bacteria deficient in ampicillin resistance (i.e., bacteria tucking the hybrid plasmid encoding for ampicillin resistance).

As a result, after subculturing three times, the rate of appearance of the bacteria deficient in ampicillin resistance was less than 1% when the subculture was curried out at 40° C. or over, whereas it amounted to 80% when the subculture was curried out at the temperatures below 40° C.

EXAMPLE 3

E. coli MT-10414 (FERM BP-1712) carrying the hybrid plasmid pYtrp6 was inoculated into 50 ml of LB-AP medium in a shouldered flask and the inoculated medium was incubated at 42° C. for 12 hours with shaking. The hybrid plasmid pYtrp6, having been obtained in the course of Reference Example 1, comprises the expression vector carrying the gene encoding for ampicillin resistance with the insertions of the trp promoter and the PAL structural gene being inserted at the downstream of the trp promoter.

Thirty milliliters of the culture of E. coli MT-10414 thus prepared was added to 1.0 l of the synthetic medium which had been autoclaved in a 2-l-volume jar for small scale fermentation and aseptically supplemented with 50 mg of ampicillin after the autoclave. The inoculated medium was then incubated with aeration and shaking.

The incubation was curried out at the incubation temperature of 42° C. for the first six hours to reach the midst of the log phase of the cell growth and then the temperature was dropped to 30° C. and thereafter, the incubation was continued for 18 hours. The pH of the culture was maintained at 7.0 throughout the incubation.

After completion of the incubation, bacterial cells were collected by centrifugation, suspended and washed in a 0.85% aqueous NaCl solution and then collected again by centrifugation. The cells thus obtained were suspended in a 0.05 M Tris-HCl buffer solution (pH 8.8) to give a cell concentration of 1% by wet weight and the cell extract was prepared in the same manner as described in Example 1. The PAL specific activity of the extract was 270 U/g cells by dry weight.

COMPARATIVE EXAMPLE 3

The cell preparation was obtained in the same manner as described in Example 3, except that the incubation temperature was 30° C. throughout the incubation. The PAL specific activity of the cells thus Obtained was 45 U/g cells by dry weight.

Furthermore, the incidence of the hybrid-deleted bacteria was examined by the aforementioned method. The rate of the bacteria deficient in ampicillin resistance after 24-hour incubation was about 85% in this case of Comparative Example 3, whereas it was only about 10% in the case of Example 3.

EXAMPLE 4

The culture of E. coli MT-10423 (FERM BP-1713) carrying the hybrid plasmid pSW115 as used in Example 1 was spread on an LB-AP agar medium plate and was incubated at 37° C.

Bacterial cells were taken up from a colony appeared on the plate and suspended in 0.5 ml of LB-AP medium in a test tube and aliquots of 50 microliters each of the suspension were dispensed into 5 test tubes each having a cotton plug and containing 5 ml of LB-AP medium therein. Each tube was incubated for 24 hours with shaking at 110 strokes per minute at one of the temperatures indicated in Table 4. Immediately after completion of the incubation, cells were collected by centrifugation, suspended and washed in a 0.85% NaCl aqueous solution. The cells were again collected by centrifugation and frozen for storage.

Subsequently, the frozen cells were defrosted and treated in the same manner as described in Example 1 to determine the PAL activity. As shown in Table 4, it was confirmed that the expression of the foreign gene could be regulated by changing the culture temperature.

Effect of culture temperature on the PAL expression in each of the following three transformants was examined by the same method as described above:

a. E. coli MT-10424 used in Example 2;
b. E. coli OMT-2206 (FERM BP-3569), which was obtained by transforming E. coli JM 105 with hybrid plasmid pSW 115 constructed in Reference example 1; and
c. E. coli OMT-2236, which was obtained by transforming E. coli JM 105 with hybrid plasmid pSYP$_L$.3 constructed in Reference example 2.

The results are shown in Table 4. The PAL expression in each transformant was regulated by changing the culture temperature.

TABLE 4

| Transformant | PAL activity (U/g cells*) Culture temperature (°C.) | | | | |
| --- | --- | --- | --- | --- | --- |
| | 30 | 33 | 37 | 40 | 45 |
| MT-10423 | 293 | 290 | 255 | 88 | 48 |
| OMT-2206 | 261 | 249 | 246 | 71 | 25 |
| MT-10424 | 198 | 192 | 180 | 42 | 12 |
| OMT-2236 | 126 | 123 | 111 | 39 | 9 |

*: by dry weight

Among the above-mentioned strains, those having an ATCC. number have been deposited with the American Type Culture Collection, 12301 Parklawn Drive, Rockville, Md. 20852-1776, U.S.A.; that having an IFO number with the Fermentation Research Institute (Incorporated Foundation), 17-85, Juso-Motomachi 2-chome, Yodogawa-ku, Osaka City, Japan; and those having an FERM number with the Fermentation Research Institute of the Agency of Industrial Science and Technology, 1-3, Higashi 1-chome, Tsukuba-shi, Ibaraki-ken, 305, Japan.

Those having an ATCC. number and that having an IFO number are publicly available.

Those having an FERM number were deposited on the following date for patent purposes under the Budapest Treaty by the applicant.

FERM BP-1710 (MT-10410) on Jul. 4, 1986;
FERM BP-1712 (MT-10414) on Jul. 26, 1986;
FERM BP-1713 (MT-10423) on Oct. 31, 1986;
FERM BP-1714 (MT-10424) on Oct. 31, 1986; and
FERM BP-3569 (OMT-2206) on Sep. 20, 1991.

What is claimed is:

1. A method of regulating the expression of a gene coding for L-phenylalanine ammonialyase isolated from *Rhodosporidium toruloides* in a bacterium of *Escherichia coli* carrying a recombinant plasmid in which the plasmid comprises a promoter selected from the group consisting of a $P_L$ lambda promoter and a combined promoter containing both the tac promoter and the $P_L$ lambda promoter, and said gene linked to said promoter so as to permit expression of said gene under the direction of said promoter, which method comprises maintaining the temperature for the culture of said *E. coli* at 40° C. or more so as to suppress the expression of said foreign gene.

2. A method of regulating the expression of a gene as claimed in claim 1, wherein the L-phenylalanine ammonialyase has the following amino acid sequence:

| 1 | | | | | | | | | 10 |
|---|---|---|---|---|---|---|---|---|---|
| Met | Ala | Pro | Ser | Leu | Asp | Ser | Ile | Ser | His |
| 11 | | | | | | | | | 20 |
| Ser | Phe | Ala | Asn | Gly | Val | Ala | Ser | Ala | Lys |
| 21 | | | | | | | | | 30 |
| Gln | Ala | Val | Asn | Gly | Ala | Ser | Thr | Asn | Leu |
| 31 | | | | | | | | | 40 |
| Ala | Val | Ala | Gly | Ser | His | Leu | Pro | Thr | Thr |
| 41 | | | | | | | | | 50 |
| Gln | Val | Thr | Gln | Val | Asp | Ile | Val | Glu | Lys |
| 51 | | | | | | | | | 60 |
| Met | Leu | Ala | Ala | Pro | Thr | Asp | Ser | Thr | Leu |
| 61 | | | | | | | | | 70 |
| Glu | Leu | Asp | Gly | Tyr | Ser | Leu | Asn | Leu | Gly |
| 71 | | | | | | | | | 80 |
| Asp | Val | Val | Ser | Ala | Ala | Arg | Lys | Gly | Arg |
| 81 | | | | | | | | | 90 |
| Pro | Val | Arg | Val | Lys | Asp | Ser | Asp | Glu | Ile |
| 91 | | | | | | | | | 100 |
| Arg | Ser | Lys | Ile | Asp | Lys | Ser | Val | Glu | Phe |
| 101 | | | | | | | | | 110 |
| Leu | Arg | Ser | Gln | Leu | Ser | Met | Ser | Val | Tyr |
| 111 | | | | | | | | | 120 |
| Gly | Val | Thr | Thr | Gly | Phe | Gly | Gly | Ser | Ala |
| 121 | | | | | | | | | 130 |
| Asp | Thr | Arg | Thr | Glu | Asp | Ala | Ile | Ser | Leu |
| 131 | | | | | | | | | 140 |
| Gln | Lys | Ala | Leu | Leu | Glu | His | Gln | Leu | Cys |
| 141 | | | | | | | | | 150 |
| Gly | Val | Leu | Pro | Ser | Ser | Phe | Asp | Ser | Phe |
| 151 | | | | | | | | | 160 |
| Arg | Leu | Gly | Arg | Gly | Leu | Glu | Asn | Ser | Leu |
| 161 | | | | | | | | | 170 |
| Pro | Leu | Glu | Val | Val | Arg | Gly | Ala | Met | Thr |
| 171 | | | | | | | | | 180 |
| Ile | Arg | Val | Asn | Ser | Leu | Thr | Arg | Gly | His |
| 181 | | | | | | | | | 190 |
| Ser | Ala | Val | Arg | Leu | Val | Val | Leu | Glu | Ala |
| 191 | | | | | | | | | 200 |
| Leu | Thr | Asn | Phe | Leu | Asn | His | Gly | Ile | Thr |
| 201 | | | | | | | | | 210 |
| Pro | Ile | Val | Pro | Leu | Arg | Gly | Thr | Ile | Ser |
| 211 | | | | | | | | | 220 |
| Ala | Ser | Gly | Asp | Leu | Ser | Pro | Leu | Ser | Tyr |
| 221 | | | | | | | | | 230 |
| Ile | Ala | Ala | Ala | Ile | Ser | Gly | His | Pro | Asp |
| 231 | | | | | | | | | 240 |
| Ser | Lys | Val | His | Val | Val | His | Glu | Gly | Lys |
| 241 | | | | | | | | | 250 |
| Glu | Lys | Ile | Leu | Tyr | Ala | Arg | Glu | Ala | Met |
| 251 | | | | | | | | | 260 |
| Ala | Leu | Phe | Asn | Leu | Glu | pro | Val | Val | Leu |
| 261 | | | | | | | | | 270 |
| Gly | Pro | Lys | Glu | Gly | Leu | Gly | Leu | Val | Asn |
| 271 | | | | | | | | | 280 |
| Gly | Thr | Ala | Val | Ser | Ala | Ser | Met | Ala | Thr |
| 281 | | | | | | | | | 290 |
| Leu | Ala | Leu | His | Asp | Ala | His | Met | Leu | Ser |
| 291 | | | | | | | | | 300 |
| Leu | Leu | Ser | Gln | Ser | Leu | Thr | Ala | Met | Thr |
| 301 | | | | | | | | | 310 |
| Val | Glu | Ala | Met | Val | Gly | His | Ala | Gly | Ser |
| 311 | | | | | | | | | 320 |
| Phe | His | Pro | Phe | Leu | His | Asp | Val | Thr | Arg |
| 321 | | | | | | | | | 330 |
| Pro | His | Pro | Thr | Gln | Ile | Glu | Val | Ala | Gly |
| 331 | | | | | | | | | 340 |
| Asn | Ile | Arg | Lys | Leu | Leu | Glu | Gly | Ser | Arg |
| 341 | | | | | | | | | 350 |
| Phe | Ala | Val | His | His | Glu | Glu | Glu | Val | Lys |
| 351 | | | | | | | | | 360 |
| Val | Lys | Asp | Asp | Glu | Gly | Ile | Leu | Arg | Gln |
| 361 | | | | | | | | | 370 |
| Asp | Arg | Tyr | Pro | Leu | Arg | Thr | Ser | Pro | Gln |
| 371 | | | | | | | | | 380 |
| Trp | Leu | Gly | pro | Leu | Val | Ser | Asp | Leu | Ile |
| 381 | | | | | | | | | 390 |
| His | Ala | His | Ala | Val | Leu | Thr | Ile | Glu | Ala |
| 391 | | | | | | | | | 400 |
| Gly | Gln | Ser | Thr | Thr | Asp | Asn | Pro | Leu | Ile |
| 401 | | | | | | | | | 410 |
| Asp | Val | Glu | Asn | Lys | Thr | Ser | His | His | Gly |
| 411 | | | | | | | | | 420 |
| Gly | Asn | Phe | Gln | Ala | Ala | Ala | Val | Ala | Asn |
| 421 | | | | | | | | | 430 |
| Thr | Met | Glu | Lys | Thr | Arg | Leu | Gly | Leu | Ala |
| 431 | | | | | | | | | 440 |
| Gln | Ile | Gly | Lys | Leu | Asn | Phe | Thr | Gln | Leu |
| 441 | | | | | | | | | 450 |
| Thr | Glu | Met | Leu | Asn | Ala | Gly | Met | Asn | Arg |
| 451 | | | | | | | | | 460 |
| Gly | Leu | Pro | Ser | Cys | Leu | Ala | Ala | Glu | Asp |
| 461 | | | | | | | | | 470 |
| Pro | Ser | Leu | Ser | Tyr | His | Cys | Lys | Gly | Leu |
| 471 | | | | | | | | | 480 |
| Asp | Ile | Ala | Ala | Ala | Ala | Tyr | Thr | Ser | Glu |
| 481 | | | | | | | | | 490 |
| Leu | Gly | His | Leu | Ala | Asn | Pro | Val | Thr | Thr |
| 491 | | | | | | | | | 500 |
| His | Val | Gln | Pro | Ala | Glu | Met | Ala | Asn | Gln |
| 501 | | | | | | | | | 510 |
| Ala | Val | Asn | Ser | Leu | Ala | Leu | Ile | Ser | Ala |
| 511 | | | | | | | | | 520 |
| Arg | Arg | Thr | Thr | Glu | Ser | Asn | Asp | Val | Leu |
| 521 | | | | | | | | | 530 |
| Ser | Leu | Leu | Leu | Ala | Thr | His | Leu | Tyr | Cys |
| 531 | | | | | | | | | 540 |
| Val | Leu | Gln | Ala | Ile | Asp | Leu | Arg | Ala | Ile |
| 541 | | | | | | | | | 550 |
| Glu | Phe | Glu | Phe | Lys | Lys | Gln | Phe | Gly | Pro |
| 551 | | | | | | | | | 560 |
| Ala | Ile | Val | Ser | Leu | Ile | Asp | Gln | His | Phe |
| 561 | | | | | | | | | 570 |
| Gly | Ser | Ala | Met | Thr | Gly | Ser | Asn | Leu | Arg |
| 571 | | | | | | | | | 580 |
| Asp | Glu | Leu | Val | Glu | Lys | Val | Asn | Lys | Thr |
| 581 | | | | | | | | | 590 |
| Leu | Ala | Lys | Arg | Leu | Glu | Gln | Thr | Asn | Ser |
| 591 | | | | | | | | | 600 |
| Tyr | Asp | Leu | Val | Pro | Arg | Trp | His | Asp | Ala |
| 601 | | | | | | | | | 610 |
| Phe | Ser | Phe | Ala | Ala | Gly | Thr | Val | Val | Glu |
| 611 | | | | | | | | | 620 |
| Val | Leu | Ser | Ser | Thr | Ser | Leu | Ser | Leu | Ala |

| | | | | | | | | | |
|---|---|---|---|---|---|---|---|---|---|
| 621 | | | | | | | | | 630 |
| Ala | Val | Asn | Ala | Trp | Lys | Val | Ala | Ala | Ala |
| 631 | | | | | | | | | 640 |
| Glu | Ser | Ala | Ile | Ser | Leu | Thr | Arg | Gln | Val |
| 641 | | | | | | | | | 650 |
| Arg | Glu | Thr | Phe | Trp | Ser | Ala | Ala | Ser | Thr |
| 651 | | | | | | | | | 660 |
| Ser | Ser | Pro | Ala | Leu | Ser | Tyr | Leu | Ser | Pro |
| 661 | | | | | | | | | 670 |
| Arg | Thr | Gln | Ile | Leu | Tyr | Ala | Phe | Val | Arg |
| 671 | | | | | | | | | 680 |
| Glu | Glu | Leu | Gly | Val | Lys | Ala | Arg | Arg | Gly |
| 681 | | | | | | | | | 690 |
| Asp | Val | Phe | Leu | Gly | Lys | Gln | Glu | Val | Thr |
| 691 | | | | | | | | | 700 |
| Ile | Gly | Ser | Asn | Val | Ser | Lys | Ile | Tyr | Glu |
| 701 | | | | | | | | | 710 |
| Ala | Ile | Lys | Ser | Gly | Arg | Ile | Asn | Asn | Val |
| 711 | | | | | 716 | | | | |
| Leu | Leu | Lys | Met | Leu | Ala | | | | |

3. A method of regulating the expression of a gene as claimed in claim 1, wherein said *Escherichia coli* has all of the identifying characteristics of OMT-2206, OMT-2236, MT-10424 or MT-10423.

4. A process of producing a gene product which is L-phenylalanine ammonialyase encoded by a gene isolated from *Rhodosporidium toruloides* by culturing *Escherichia coli* carrying a recombinant plasmid in which the plasmid comprises a promoter selected from the group consisting of a $P_L$ lambda promoter and a combined promoter containing both the tac promoter and the $P_L$ promoter, and said gene linked to said promoter so as to permit expression of said gene under the direction of said promoter, which comprises the steps of:
(a) culturing said *Escherichia coli* at a temperature of at least 40° C., and thereafter
(b) culturing the *Escherichia coli* grown in step (a) at a temperature below 40° C.

5. A process of producing a gene product as claimed in claim 4, wherein the L-phenylalanine ammonialyase has the following amino acid sequence:

| | | | | | | | | | |
|---|---|---|---|---|---|---|---|---|---|
| 1 | | | | | | | | | 10 |
| Met | Ala | Pro | Ser | Leu | Asp | Ser | Ile | Ser | His |
| 11 | | | | | | | | | 20 |
| Ser | Phe | Ala | Asn | Gly | Val | Ala | Ser | Ala | Lys |
| 21 | | | | | | | | | 30 |
| Gln | Ala | Val | Asn | Gly | Ala | Ser | Thr | Asn | Leu |
| 31 | | | | | | | | | 40 |
| Ala | Val | Ala | Gly | Ser | His | Leu | Pro | Thr | Thr |
| 41 | | | | | | | | | 50 |
| Gln | Val | Thr | Gln | Val | Asp | Ile | Val | Glu | Lys |
| 51 | | | | | | | | | 60 |
| Met | Leu | Ala | Ala | Pro | Thr | Asp | Ser | Thr | Leu |
| 61 | | | | | | | | | 70 |
| Glu | Leu | Asp | Gly | Tyr | Ser | Leu | Asn | Leu | Gly |
| 71 | | | | | | | | | 80 |
| Asp | Val | Val | Ser | Ala | Ala | Arg | Lys | Gly | Arg |
| 81 | | | | | | | | | 90 |
| Pro | Val | Arg | Val | Lys | Asp | Ser | Asp | Glu | Ile |
| 91 | | | | | | | | | 100 |
| Arg | Ser | Lys | Ile | Asp | Lys | Ser | Val | Glu | Phe |
| 101 | | | | | | | | | 110 |
| Leu | Arg | Ser | Gln | Leu | Ser | Met | Ser | Val | Tyr |
| 111 | | | | | | | | | 120 |
| Gly | Val | Thr | Thr | Gly | Phe | Gly | Gly | Ser | Ala |
| 121 | | | | | | | | | 130 |
| Asp | Thr | Arg | Thr | Glu | Asp | Ala | Ile | Ser | Leu |
| 131 | | | | | | | | | 140 |
| Gln | Lys | Ala | Leu | Leu | Glu | His | Gln | Leu | Cys |
| 141 | | | | | | | | | 150 |
| Gly | Val | Leu | Pro | Ser | Ser | Phe | Asp | Ser | Phe |
| 151 | | | | | | | | | 160 |
| Arg | Leu | Gly | Arg | Gly | Leu | Glu | Asn | Ser | Leu |
| 161 | | | | | | | | | 170 |
| Pro | Leu | Glu | Val | Val | Arg | Gly | Ala | Met | Thr |
| 171 | | | | | | | | | 180 |
| Ile | Arg | Val | Asn | Ser | Leu | Thr | Arg | Gly | His |
| 181 | | | | | | | | | 190 |
| Ser | Ala | Val | Arg | Leu | Val | Val | Leu | Glu | Ala |
| 191 | | | | | | | | | 200 |
| Leu | Thr | Asn | Phe | Leu | Asn | His | Gly | Ile | Thr |
| 201 | | | | | | | | | 210 |
| Pro | Ile | Val | Pro | Leu | Arg | Gly | Thr | Ile | Ser |
| 211 | | | | | | | | | 220 |
| Ala | Ser | Gly | Asp | Leu | Ser | Pro | Leu | Ser | Tyr |
| 221 | | | | | | | | | 230 |
| Ile | Ala | Ala | Ala | Ile | Ser | Gly | His | Pro | Asp |
| 231 | | | | | | | | | 240 |
| Ser | Lys | Val | His | Val | Val | His | Glu | Gly | Lys |
| 241 | | | | | | | | | 250 |
| Glu | Lys | Ile | Leu | Tyr | Ala | Arg | Glu | Ala | Met |
| 251 | | | | | | | | | 260 |
| Ala | Leu | Phe | Asn | Leu | Glu | pro | Val | Val | Leu |
| 261 | | | | | | | | | 270 |
| Gly | Pro | Lys | Glu | Gly | Leu | Gly | Leu | Val | Asn |
| 271 | | | | | | | | | 280 |
| Gly | Thr | Ala | Val | Ser | Ala | Ser | Met | Ala | Thr |
| 281 | | | | | | | | | 290 |
| Leu | Ala | Leu | His | Asp | Ala | His | Met | Leu | Ser |
| 291 | | | | | | | | | 300 |
| Leu | Leu | Ser | Gln | Ser | Leu | Thr | Ala | Met | Thr |
| 301 | | | | | | | | | 310 |
| Val | Glu | Ala | Met | Val | Gly | His | Ala | Gly | Ser |
| 311 | | | | | | | | | 320 |
| Phe | His | Pro | Phe | Leu | His | Asp | Val | Thr | Arg |
| 321 | | | | | | | | | 330 |
| Pro | His | Pro | Thr | Gln | Ile | Glu | Val | Ala | Gly |
| 331 | | | | | | | | | 340 |
| Asn | Ile | Arg | Lys | Leu | Leu | Glu | Gly | Ser | Arg |
| 341 | | | | | | | | | 350 |
| Phe | Ala | Val | His | His | Glu | Glu | Glu | Val | Lys |
| 351 | | | | | | | | | 360 |
| Val | Lys | Asp | Asp | Glu | Gly | Ile | Leu | Arg | Gln |
| 361 | | | | | | | | | 370 |
| Asp | Arg | Tyr | Pro | Leu | Arg | Thr | Ser | Pro | Gln |
| 371 | | | | | | | | | 380 |
| Trp | Leu | Gly | pro | Leu | Val | Ser | Asp | Leu | Ile |
| 381 | | | | | | | | | 390 |
| His | Ala | His | Ala | Val | Leu | Thr | Ile | Glu | Ala |
| 391 | | | | | | | | | 400 |
| Gly | Gln | Ser | Thr | Thr | Asp | Asn | Pro | Leu | Ile |
| 401 | | | | | | | | | 410 |
| Asp | Val | Glu | Asn | Lys | Thr | Ser | His | His | Gly |
| 411 | | | | | | | | | 420 |
| Gly | Asn | Phe | Gln | Ala | Ala | Ala | Val | Ala | Asn |
| 421 | | | | | | | | | 430 |
| Thr | Met | Glu | Lys | Thr | Arg | Leu | Gly | Leu | Ala |
| 431 | | | | | | | | | 440 |
| Gln | Ile | Gly | Lys | Leu | Asn | Phe | Thr | Gln | Leu |
| 441 | | | | | | | | | 450 |
| Thr | Glu | Met | Leu | Asn | Ala | Gly | Met | Asn | Arg |
| 451 | | | | | | | | | 460 |
| Gly | Leu | Pro | Ser | Cys | Leu | Ala | Ala | Glu | Asp |
| 461 | | | | | | | | | 470 |
| Pro | Ser | Leu | Ser | Tyr | His | Cys | Lys | Gly | Leu |
| 471 | | | | | | | | | 480 |
| Asp | Ile | Ala | Ala | Ala | Ala | Tyr | Thr | Ser | Glu |
| 481 | | | | | | | | | 490 |
| Leu | Gly | His | Leu | Ala | Asn | Pro | Val | Thr | Thr |
| 491 | | | | | | | | | 500 |
| His | Val | Gln | Pro | Ala | Glu | Met | Ala | Asn | Gln |
| 501 | | | | | | | | | 510 |
| Ala | Val | Asn | Ser | Leu | Ala | Leu | Ile | Ser | Ala |
| 511 | | | | | | | | | 520 |
| Arg | Arg | Thr | Thr | Glu | Ser | Asn | Asp | Val | Leu |
| 521 | | | | | | | | | 530 |
| Ser | Leu | Leu | Leu | Ala | Thr | His | Leu | Tyr | Cys |
| 531 | | | | | | | | | 540 |
| Val | Leu | Gln | Ala | Ile | Asp | Leu | Arg | Ala | Ile |
| 541 | | | | | | | | | 550 |
| Glu | Phe | Glu | Phe | Lys | Lys | Gln | Phe | Gly | Pro |
| 551 | | | | | | | | | 560 |
| Ala | Ile | Val | Ser | Leu | Ile | Asp | Gln | His | Phe |
| 561 | | | | | | | | | 570 |
| Gly | Ser | Ala | Met | Thr | Gly | Ser | Asn | Leu | Arg |

-continued

| 571 | | | | | | | | | 580 |
|---|---|---|---|---|---|---|---|---|---|
| Asp | Glu | Leu | Val | Glu | Lys | Val | Asn | Lys | Thr |
| 581 | | | | | | | | | 590 |
| Leu | Ala | Lys | Arg | Leu | Glu | Gln | Thr | Asn | Ser |
| 591 | | | | | | | | | 600 |
| Tyr | Asp | Leu | Val | Pro | Arg | Trp | His | Asp | Ala |
| 601 | | | | | | | | | 610 |
| Phe | Ser | Phe | Ala | Ala | Gly | Thr | Val | Val | Glu |
| 611 | | | | | | | | | 620 |
| Val | Leu | Ser | Ser | Thr | Ser | Leu | Ser | Leu | Ala |
| 621 | | | | | | | | | 630 |
| Ala | Val | Asn | Ala | Trp | Lys | Val | Ala | Ala | Ala |
| 631 | | | | | | | | | 640 |
| Glu | Ser | Ala | Ile | Ser | Leu | Thr | Arg | Gln | Val |
| 641 | | | | | | | | | 650 |
| Arg | Glu | Thr | Phe | Trp | Ser | Ala | Ala | Ser | Thr |
| 651 | | | | | | | | | 660 |
| Ser | Ser | Pro | Ala | Leu | Ser | Tyr | Leu | Ser | Pro |

-continued

| 661 | | | | | | | | | 670 |
|---|---|---|---|---|---|---|---|---|---|
| Arg | Thr | Gln | Ile | Leu | Tyr | Ala | Phe | Val | Arg |
| 671 | | | | | | | | | 680 |
| Glu | Glu | Leu | Gly | Val | Lys | Ala | Arg | Arg | Gly |
| 681 | | | | | | | | | 690 |
| Asp | Val | Phe | Leu | Gly | Lys | Gln | Glu | Val | Thr |
| 691 | | | | | | | | | 700 |
| Ile | Gly | Ser | Asn | Val | Ser | Lys | Ile | Tyr | Glu |
| 701 | | | | | | | | | 710 |
| Ala | Ile | Lys | Ser | Gly | Arg | Ile | Asn | Asn | Val |
| 711 | | | | | 716 | | | | |
| Leu | Leu | Lys | Met | Leu | Ala | | | | |

6. A process as claimed in claim 4, wherein said *Escherichia coli* has all of the identifying characteristics of OMT-2206, OMT-2236, MT-10424 or MT-10423. PAL of *Rhodosporidium toruloides* in Reference Example 1, was

* * * * *